US006982170B1

(12) United States Patent
Maciag et al.

(10) Patent No.: US 6,982,170 B1
(45) Date of Patent: Jan. 3, 2006

(54) COMPOSITIONS, METHODS AND KITS RELATING TO THROMBIN DEGRADATION RESISTANT FIBROBLAST GROWTH FACTOR-1

(75) Inventors: Thomas Maciag, Freeport, ME (US); David S. Ettenson, Somerville, MA (US); Wilson H. Burgess, Clifton, VA (US); William N. Drohan, Springfield, VA (US)

(73) Assignees: Maine Medical Center Research Institute, Searborough, ME (US); Repair, Inc., Portland, ME (US)

( * ) Notice: Subject to any disclaimer, the term of this patent is extended or adjusted under 35 U.S.C. 154(b) by 0 days.

(21) Appl. No.: 10/022,554

(22) Filed: Dec. 17, 2001

(51) Int. Cl.
*C12N 15/85* (2006.01)
(52) U.S. Cl. .................... 435/325; 435/23.1; 536/23.5
(58) Field of Classification Search ............... 435/325, 435/252.3; 536/23.1; 530/350
See application file for complete search history.

(56) References Cited

U.S. PATENT DOCUMENTS

| 4,868,113 | A | 9/1989 | Jaye et al. |
| 5,552,528 | A | 9/1996 | Burgess et al. |
| 5,571,790 | A | 11/1996 | Jaye et al. |
| 5,827,826 | A | 10/1998 | Jaye et al. |
| 5,849,538 | A | 12/1998 | Jaye et al. |
| 6,117,425 | A | 9/2000 | MacPhee et al. |

FOREIGN PATENT DOCUMENTS

| WO | WO 92/09301 | 6/1992 |
| WO | WO 94/20133 | 9/1994 |

OTHER PUBLICATIONS

Shireman, P. et al. The S130K fibroblast growth factor-1 mutant induces heparin-independent proliferation and is resistant to thrombin degradation in fibrin glue. Journal of Vascular Surgery, Feb. 2000, vol. 31, pp. 382-390.*
Baird, et al., 1990, In: Peptide Growth Factors and their Receptors, pp. 349-418, Sporn eds. Springer-Verlag, New York.
Bjornsson, et al., 1991, Proc. Natl. Acad. Sci. USA 88:8651-8655.
Burgess, et al., 1989, Am. Rev. Biochem 58:575-606.
Gimenez-Gallego, et al., 1986, Biochem. Biophys. Res. Comm. 138:611-617.
Lobb, 1988, Biochemistry, 27:2572-2578.
Thomas, et al., 1987, FASEB J. 1:434-440.

* cited by examiner

*Primary Examiner*—Dave Trong Nguyen
*Assistant Examiner*—Jon Eric Angell
(74) *Attorney, Agent, or Firm*—Drinker, Biddle & Reath, LLP

(57) ABSTRACT

The invention relates to novel degradation resistant FGF-1, and methods for producing and using the same. More specifically, the invention relates to identification of a thrombin degradation resistant FGF-1, an a nucleic acid encoding the same. The thrombin degradation resistant FGF-1 can elicit responses that are otherwise typically impeded by degradation of FGF-1 by thrombin. Thrombin degradation resistant FGF-1 is an important molecule for effecting an FGF-1 response that would be otherwise inhibited by thrombin. Thus, the present invention provides a powerful therapeutic for diseases or disorders wherein an FGF-1 response can mediate a reduction in the frequency or intensity of a symptom of the disease or disorder but for degradation of FGF-1 before it can effect the response.

18 Claims, 11 Drawing Sheets

GAATTCGGGAACGCGCCACAAGCAGCAGCTGCTGAGCC[ATGGCTGAAGGGAAATCACCACCTTCACAGCCCTGACCGAGAAGTTTAAT 89
                                       A  E  G  E  I  T  T  F  T  A  L  T  E  K  F  N  16

CTGCCTCCAGGGAATTACAAGAAGCCCAAACTCCTCTACTGTAGCAACGGGGCCACTTCCTGAGGATCCTTCCGGATGGCACAGTGGAT 178
 L  P  P  G  N  Y  K  K  P  K  L  L  Y  C  S  N  G  G  H  F  L  R  I  L  P  D  G  T  V  D  46

GGGACAAGGGACAGGAGCGACCAGCACATTCAGCTGCGGAAAGCGTGGGGAGGTGTATAAAGAGTACCGAGACTGGC 277
 G  T  R  D  R  S  D  Q  H  I  Q  L  S  A  E  S  V  G  E  V  Y  I  K  S  T  E  T  G  76

CAGTACTTGGCCATGGACACCGACGGGCTTTTATACGGCTCACAGACACCAAATGAGGAATGTTTGTTCCTGAAAGGCTGGGAGGAGAAC 356
 Q  Y  L  A  M  D  T  D  G  L  L  Y  G  S  Q  T  P  N  E  E  C  L  F  L  E  R  L  E  E  N  106

CATTACAACACCTATATCCAAGAAGCATGCAGAGAAGAATTGGTTTGTTGGCCTCAAGAAGAATGGAGCTGCAAACGCGGTCCTCGG 445
 H  Y  N  T  Y  I  S  K  K  H  A  E  K  N  W  F  V  G  L  K  K  N  G  S  C  K  R  G  P  R
                                                                     CAAACGCGGGTCCTAAA
                                                                                   K  136

ACTCACTATGGCCAGAAAGCAATCTTGTTCTCCCCCTGCCAGTCTCTTCTGATT]AAAGAGATCTGTTCTGGTGTTGACCACTCCAGAGA 534
 T  H  Y  G  Q  K  A  I  L  F  L  P  L  P  V  S  S  D
                                                      154

AGTTTCGAGGGTCCTCACCTGGTTGACCCCAAAAATGTTCCCTTGACCATTGGCTGCGCTAACCCCAGCCCACAGAGCCTGAATTTGT 623
 T  H  Y  G  Q  K  A  I  L  F  L  P  L  P  V  S  S  D
ACTCACTATGGCCAG

AAGCAACTT
     632

FIGURE 1

```
GAATTCGGGA ACGCGCCACA AGCAGCAGCT GCTGAGCCAT
GGCTGAAGGG GAAATCACCA CCTTCACAGC CCTGACCGAG
AAGTTTAATC TGCCTCCAGG GAATTACAAG AAGCCCAAAC
TCCTCTACTG TAGCAACGGG GGCCACTTCC TGAGGATCCT
TCCGGATGGC ACAGTGGATG GGACAAGGGA CAGGAGCGAC
CAGCACATTC AGCTGCAGCT CAGTGCGGAA AGCGTGGGGG
AGGTGTATAT AAAGAGTACC GAGACTGGCC AGTACTTGGC
CATGGACACC GACGGGCTTT TATACGGCTC ACAGACACCA
AATGAGGAAT GTTTGTTCCT GGAAGGCTG GAGGAGAACC
ATTACAACAC CTATATATCC AAGAAGCATG CAGAGAAGAA
TTGGTTTGTT GGCCTCAAGA AGAATGGGAG CTGCAAACGC
GGTCCTCGGA CTCACTATGG CCAGAAAGCA ATCTTGTTTC
TCCCCCTGCC AGTCTCTTCT GATTAAAGAG ATCTGTTCTG
GTGTTGACCA CTCCAGAGAA GTTTCGAGGG GTCCTCACCT
GGTTGACCCC AAAAATGTTC CCTTGACCAT TGGCTGCGCT
AACCCCCAGC CCACAGAGCC TGAATTTGTA AGCAACTT
```

FIGURE 8

```
AEGEITTFTA  LTEKFNLPPG  NYKKPKLLYC  SNGGHFLRIL
PDGTVDGTRD  RSDQHIQLQL  SAESVGEVYI  KSTETGQYLA
MDTDGLLYGS  QTPNEECLFL  ERLEENHYNT  YISKKHAEKN
WFVGLKKNGS  CKRGPRTHYG  QKAILFLPLP  VSSD
```

FIGURE 9

```
GAATTCGGGA ACGCGCCACA AGCAGCAGCT GCTGAGCCAT
GGCTGAAGGG GAAATCACCA CCTTCACAGC CCTGACCGAG
AAGTTTAATC TGCCTCCAGG GAATTACAAG AAGCCCAAAC
TCCTCTACTG TAGCAACGGG GGCCACTTCC TGAGGATCCT
TCCGGATGGC ACAGTGGATG GGACAAGGGA CAGGAGCGAC
CAGCACATTC AGCTGCAGCT CAGTGCGGAA AGCGTGGGGG
AGGTGTATAT AAAGAGTACC GAGACTGGCC AGTACTTGGC
CATGGACACC GACGGGCTTT TATACGGCTC ACAGACACCA
AATGAGGAAT GTTTGTTCCT GGAAGGCTG GAGGAGAACC
ATTACAACAC CTATATATCC AAGAAGCATG CAGAGAAGAA
TTGGTTTGTT GGCCTCAAGA AGAATGGGAG CTGCAAACGC
GGTCCTAAAA CTCACTATGG CCAGAAAGCA ATCTTGTTTC
TCCCCCTGCC AGTCTCTTCT GATTAAAGAG ATCTGTTCTG
GTGTTGACCA CTCCAGAGAA GTTTCGAGGG GTCCTCACCT
GGTTGACCCC AAAAATGTTC CCTTGACCAT TGGCTGCGCT
AACCCCCAGC CCACAGAGCC TGAATTTGTA AGCAACTT
```

FIGURE 10

```
AEGEITTFTA  LTEKFNLPPG  NYKKPKLLYC  SNGGHFLRIL
PDGTVDGTRD  RSDQHIQLQL  SAESVGEVYI  KSTETGQYLA
MDTDGLLYGS  QTPNEECLFL  ERLEENHYNT  YISKKHAEKN
WFVGLKKNGS  CKRGPKTHYG  QKAILFLPLP  VSSD
```

FIGURE 11

COMPOSITIONS, METHODS AND KITS RELATING TO THROMBIN DEGRADATION RESISTANT FIBROBLAST GROWTH FACTOR-1

STATEMENT REGARDING FEDERALLY SPONSORED RESEARCH OR DEVELOPMENT

This invention was supported in part by US Government funds (National Institutes of Health grant Nos. HL32348 and HL44336), and the US Government may therefore have certain rights in the invention.

BACKGROUND OF THE INVENTION

The fibroblast growth factor (FGF) family comprises over twenty structurally related proteins. These proteins exert a wide range of effects on cells of the vascular, neural, endocrine, and immune systems. That is, the FGF family proteins can induce such events as angiogenesis, regeneration, and morphogenesis. For instance, members of the FGF family have been implicated in such processes as, but not limited to, cell migration, proliferation, and differentiation (Burgess and Maciag 1989, Ann. Rev. Biochem. 58:575; Thomas, 1987, FASEB J. 1:434; Baird and Bohlen, 1990, In: Peptide Growth Factors and their Receptors, pp. 369–418, Sporn et al., eds., Springer-Verlag, New York; Bjornsson et al., 1991, Proc. Natl. Acad. Sci. USA 88:8651).

Moreover, members of the FGF family are potent regulators of developmental, physiological and pathophysiologic events in mammals. Therefore, these are important molecules in the development of therapeutics relating to these events.

The most well-studied members of the FGF family are FGF-1 and FGF-2, which have been referred to under various names, most often as acidic FGF and basic FGF, respectively. Both factors have been characterized extensively as described, for instance, in U.S. Pat. No. 5,849,538, U.S. Pat. No. 5,827,826, U.S. Pat. No. 5,571,790, U.S. Pat. No. 5,552,528, and U.S. Pat. No. 4,868,113.

Although there is a large overlap in the spectrum of receptor-binding properties and biological activities shared among the FGFs, the only known function shared by all members of the family is a relatively high affinity for heparin or heparan sulfate. It has also been demonstrated that binding with heparin can potentiate the mitogenic activity of FGF-1 and can protect both FGF-1 and FGF-2 from inactivation by proteolysis and heat.

As peptide growth factors, the mitogenic activities of FGFs are mediated by a high affinity receptor located at the plasma membrane. Numerous reports have shown that FGF-1 has potent angiogenic activity and nerve regeneration inducing ability. Angiogenesis and nerve regeneration are two events that must occur following injury to restore the tissue to a normal functional state following injury. Thus, FGF-1 has the potential to be used as a therapeutic agent to promote such events as angiogenesis and nerve regeneration. For example, FGF-1 is a good candidate to promote angiogenesis in the heart following myocardial ischemia.

Despite the important role of FGF-1 in mediating repair of tissue injury, studies where FGF-1 was administered by intravenous and intracoronary techniques to induce angiogenesis in an injured heart were not particularly successful. This failure was primarily due to insufficient amounts of biologically active FGF-1 reaching the designated target area. Without wishing to be bound by any particular theory, these failures have been thought to be due in part to the proteolytic degradation of FGF-1 before it can reach the ischemic area. Thus, a more protease resistant, or degradation resistant, form of FGF-1 would significantly enhance the therapeutic potential of FGF-1.

More specifically, therapeutic use of native or wild-type FGF-1 (wt FGF-1) has been impeded because it is susceptible to cleavage by thrombin (Lobb, 1988, Biochemistry 27:2572). This is particularly important in wound healing, repair, and angiogenesis because of the intimate anatomical relationship between nerves and vasculature such that tissue injury results in concurrent damage to both the neural and vascular systems and the damaged area is generally embedded in a fibrin clot. Because much of the thrombin generated during coagulation associates with fibrin, high concentrations of thrombin are typically present at the site of injury. Under such conditions, FGF-1 is rapidly cleaved to smaller biologically less active and/or inactive fragments due to thrombin degradation. Thus, thrombin degradation inhibits the therapeutic effects of FGF-1 at the site of injury.

To date, prior art methods for administration of FGF-1 to a site of interest have not considered protecting it from thrombin degradation and have been unsuccessful. In addition, a potential way of delivering FGF-1 locally to the site of injury involves its incorporation into fibrin sealant. Fibrin sealant, as disclosed in, e.g., International Publication No. WO 92/09301, and WO 94/20133, and U.S. Pat. No. 6,117,425, can comprise a fibrinogen solution comprising plasma components such as, but not limited to, fibrinogen and factor XIII, as well as thrombin to which calcium ions are added. Equal volumes of fibrinogen and thrombin solutions are mixed together prior to use and a resulting fibrin polymer seal forms. Thrombin catalyzes the release of fibrinopeptides A and B from fibrinogen to produce fibrin monomers, which aggregate to form fibrin filaments. Thrombin also activates the transglutaminase, factor XIIIa, which catalyzes the formation of isopeptide bonds to covalently cross-link the fibrin filaments. This procedure can be modified to be used as a prolong delivery device. Growth factors, which bind to fibrin, are added to the fibrinogen solution. The resulting fibrin polymer can therefore comprise bound growth factor and, as the fibrin is degraded by naturally occurring enzymes, the growth factors would be released into the surrounding area. More specifically, WO 92/09301, WO 94/20133, and U.S. Pat. No. 6,117,425, demonstrate that FGF-1 in the presence or absence of heparin, can be mixed with fibrinogen before the addition of thrombin. Thrombin cleaved fibrinogen into fibrin thereby producing a fibrin matrix containing the FGF-1 and heparin. As the body's fibrinolytic system slowly degraded the fibrin matrix, the growth factor and heparin were expected to be released by this system.

Unfortunately, the addition of thrombin to the system degrades the FGF-1, requiring high concentrations of FGF-1 to be added in order to ensure that enough intact, active FGF-1 remained available to be released at the target site. Therefore, the fibrin sealant system, while potentially useful for sustained delivery of other growth factors, which are not susceptible to thrombin degradation, is currently not optimized for delivery of FGF-1. Thus, while a thrombin-resistant form of FGF-1 could be administered via the fibrin sealant system, such an FGF-1 is not available.

In conclusion, there is a long-felt need for methods of delivering active FGF-1 to a site of interest thereby promoting processes such as angiogenesis, nerve regeneration, and wound repair, among others. Further, there is a long-standing need for FGF-1 resistant to thrombin degradation. The present invention meets these needs.

SUMMARY OF THE INVENTION

The invention includes an isolated nucleic acid encoding a fibroblast growth factor-1 resistant to thrombin degradation, wherein the nucleic acid comprises the sequence of SEQ ID NO:3.

The invention also includes an isolated nucleic acid encoding a fibroblast growth factor-1 resistant to thrombin degradation, wherein the nucleic acid comprises the sequence of SEQ ID NO: 1 and further wherein the triplet set of nucleotides CGG at position number 443 to 445 in SEQ ID NO: 1 is substituted with a triplet set of nucleotides selected from the group consisting of AAA and AAG.

The invention includes an isolated nucleic acid encoding a fibroblast growth factor-1 resistant to thrombin degradation, wherein the nucleic acid comprises the sequence of SEQ ID NO: 1 and further wherein the triplet set of nucleotides CGG at position number 443 to 445 in SEQ ID NO: 1 is substituted with the triple set of nucleotides AAA.

The invention further includes an isolated nucleic acid encoding a fibroblast growth factor-1 resistant to thrombin degradation, wherein the nucleic acid comprises the sequence of SEQ ID NO: 1 and further wherein the triplet set of nucleotides at position number 443 to 445 in SEQ ID NO: 1 is not CGG, CGT, CGC, CGA, AGA, or AGG.

The invention includes an isolated nucleic acid encoding a fibroblast growth factor-1 resistant to thrombin degradation, wherein the nucleic acid consists of the sequence of SEQ ID NO:3.

The invention includes an isolated nucleic acid encoding a fibroblast growth factor-1 resistant to thrombin degradation, wherein the nucleic acid encodes a polypeptide comprising the amino acid sequence of SEQ ID NO:4.

The invention also includes an isolated nucleic acid encoding a fibroblast growth factor-1 resistant to thrombin degradation, wherein the nucleic acid encodes a polypeptide wherein the amino acid residue at position number 136 in SEQ ID NO:2 is lysine.

The invention includes an isolated nucleic acid encoding a fibroblast growth factor-1 resistant to thrombin degradation, wherein the nucleic acid encodes a polypeptide wherein the amino acid residue at position number 136 of SEQ ID NO:2 is not arginine.

The invention includes an isolated nucleic acid encoding a fibroblast growth factor-1 resistant to thrombin degradation, wherein the nucleic acid encodes a polypeptide consisting of the amino acid sequence of SEQ ID NO:4.

In one aspect, the nucleic acid comprises a nucleic acid specifying a promoter/regulatory sequence operably linked thereto.

In another aspect, the invention includes a vector comprising an isolated nucleic acid encoding a fibroblast growth factor-1 resistant to thrombin degradation, wherein the nucleic acid comprises the sequence of SEQ ID NO:3.

In yet another aspect, the vector further comprises a nucleic acid specifying a promoter/regulatory sequence operably linked thereto.

The invention includes a recombinant cell comprising a vector comprising an isolated nucleic acid encoding a fibroblast growth factor-1 resistant to thrombin degradation, wherein the nucleic acid comprises the sequence of SEQ ID NO:3. In one aspect, the cell is selected from a prokaryotic cell, and a eukaryotic cell.

The invention also includes a recombinant cell comprising a vector comprising an isolated nucleic acid encoding a fibroblast growth factor-1 resistant to thrombin degradation, wherein the nucleic acid comprises the sequence of SEQ ID NO:3, and the vector further comprises a nucleic acid specifying a promoter/regulatory sequence operably linked thereto.

The invention includes a recombinant cell comprising an isolated nucleic acid encoding a fibroblast growth factor-1 resistant to thrombin degradation, wherein the nucleic acid comprises the sequence of SEQ ID NO:3. In one aspect, the recombinant cell is a mammalian cell.

The invention includes a transgenic non-human mammal comprising an isolated nucleic acid encoding a fibroblast growth factor-1 resistant to thrombin degradation, wherein the nucleic acid comprises the sequence of SEQ ID NO:3.

The invention includes a transgenic non-human mammal comprising an isolated nucleic acid encoding a fibroblast growth factor-1 resistant to thrombin degradation, wherein said nucleic acid consists of the sequence of SEQ ID NO:3.

The invention also includes an isolated polypeptide encoded by an isolated nucleic acid encoding a fibroblast growth factor-1 resistant to thrombin degradation, wherein the nucleic acid comprises the sequence of SEQ ID NO:3, or a fragment or derivative thereof.

The invention includes an isolated fibroblast growth factor-1 polypeptide comprising the amino acid sequence of SEQ ID NO:4, or a fragment or derivative thereof. In one aspect, the polypeptide comprises from about amino acid 14 to amino acid residue 154 relative to SEQ ID NO:4.

In another aspect, the polypeptide comprises from about amino acid 15 to amino acid residue 154 relative to SEQ ID NO:4.

In yet another aspect, the polypeptide is resistant to thrombin degradation, and further wherein the polypeptide does not comprise an arginine amino acid residue at amino acid number 136 relative to SEQ ID NO:4.

In yet a further aspect, the polypeptide is resistant to thrombin degradation, and further wherein the polypeptide comprises a lysine amino acid residue at amino acid number 136 relative to SEQ ID NO:4.

The invention includes an isolated fibroblast growth factor-1 polypeptide consisting of the amino acid sequence of SEQ ID NO:4.

The invention also includes a composition comprising an isolated nucleic acid encoding a fibroblast growth factor-1 resistant to thrombin degradation, wherein the nucleic acid comprises the sequence of SEQ ID NO:3, or fragment, or derivative thereof, and a pharmaceutically acceptable carrier.

The invention includes a composition comprising an isolated fibroblast growth factor-1 polypeptide comprising the amino acid sequence of SEQ ID NO:4, or fragment, or derivative thereof, and a pharmaceutically acceptable carrier.

The invention includes an antibody that specifically binds with a fibroblast growth factor-1 polypeptide comprising the amino acid sequence of SEQ ID NO:4, or fragment, or derivative thereof.

In one aspect, the antibody is selected from the group consisting of a polyclonal antibody, a monoclonal antibody, a humanized antibody, a chimeric antibody, and a synthetic antibody.

The invention also includes an antibody that specifically binds with a polypeptide encoded by an isolated nucleic acid encoding a fibroblast growth factor-1 resistant to thrombin degradation, wherein the nucleic acid comprises the sequence of SEQ ID NO:3, or a fragment or derivative thereof.

The invention includes a composition comprising an antibody that specifically binds with an isolated mutant fibroblast growth factor-1 polypeptide comprising the amino acid sequence of SEQ ID NO:4, or a fragment or derivative thereof, and a pharmaceutically-acceptable carrier.

The invention includes a method of treating a disease or disorder responsive to administration of fibroblast growth factor 1 (FGF-1) in a mammal. The method comprises administering to the mammal an effective amount of a FGF-1 resistant to thrombin degradation, or a fragment or derivative thereof, thereby treating a disease or disorder responsive to administration of FGF-1 in a mammal.

In one aspect, the degradation resistant FGF-1 is FGF-$1_{R136K}$.

In another aspect, the amino acid sequence of the FGF-$1_{R136K}$ consists of SEQ ID NO:4.

In yet a further aspect, the disease or disorder is selected from the group consisting of myocardial ischemia, peripheral vascular disease, cerebral ischemia, epithelial injury, epidermal wound injury, nerve injury, and bone damage.

The invention includes a method of enhancing the effectiveness of an FGF-1 response in a mammal wherein the activity of wild-type FGF-1 degraded by thrombin. The method comprises administering to the mammal an effective amount of a thrombin degradation resistant FGF-1, or a fragment or derivative thereof, thereby enhancing the FGF-1 response in a mammal.

In one aspect, the FGF-1 response is selected from the group consisting of a vascular response, a neural response, a regeneration response, a wound healing response, and an endocrine response.

In another aspect, the thrombin degradation resistant FGF-1 is FGF-$1_{R136K}$.

The invention also includes a method of stimulating an FGF-1 response in a mammal, wherein the response is inhibited by thrombin degradation of FGF-1. The method comprises administering an effective dose of a thrombin degradation resistant FGF-1, or a fragment or derivative thereof, to the mammal, thereby stimulating an FGF-1 response in a mammal, wherein the response is otherwise inhibited by thrombin degradation of FGF-1.

In one aspect, the thrombin degradation resistant FGF-1 is FGF-$1_{R136K}$.

The invention includes a kit for treating a disease or disorder responsive to administration of FGF-1 in a mammal. The kit comprises an effective amount of a thrombin degradation resistant FGF-1, or a fragment or derivative thereof, the kit further comprising an applicator, and an instructional material for the use thereof.

In one aspect, the disease or disorder is selected from the group consisting of myocardial ischemia, peripheral vascular disease, cerebral ischemia, epithelial injury, epidermal wound injury, nerve injury, and bone damage. In another aspect, the thrombin degradation resistant FGF-1 is FGF-$1_{R136K}$.

The invention includes a kit for enhancing the effectiveness of an FGF-1 response in a mammal wherein the activity of wild-type FGF-1 is degraded by thrombin. The kit comprises an effective amount of a thrombin degradation resistant FGF-1, or a fragment or derivative thereof, the kit further comprising an applicator, and an instructional material for the use thereof. In one aspect, the thrombin degradation resistant FGF-1 is FGF-$1_{R136K}$.

The invention includes a kit for stimulating an FGF-1 response in a mammal, wherein the response is inhibited by thrombin degradation of FGF-1. The kit comprises an effective dose of a thrombin degradation resistant FGF-1, or a fragment or derivative thereof, the kit further comprising an applicator, and an instructional material for the use thereof. In one aspect, the thrombin degradation resistant FGF-1 is FGF-$1_{R136K}$.

BRIEF DESCRIPTION OF THE SEVERAL VIEWS OF THE DRAWINGS

For the purpose of illustrating the invention, there are depicted in the drawings certain embodiments of the invention. However, the invention is not limited to the precise arrangements and instrumentalities of the embodiments depicted in the drawings.

FIG. 1 provides the nucleic acid (SEQ ID NO: 1) and amino acid (SEQ ID NO:2) sequences of human wild type FGF-1 (wt FGF-1) and the nucleic acid (SEQ ID NO:3) and amino acid (SEQ ID NO:4) sequences of thrombin resistant FGF-$1_{R136K}$. The nucleic acid coding sequence that is translated into each FGF-1 protein is shown between the square brackets. The amino acid sequence is located below each codon encoding the respective amino acid residue. The full length human FGF-1 DNA sequence encodes a 154 amino acid form of the FGF-1 protein, not counting the initial methionine encoded by the canonical start codon (AUG).

FGF-1 can also exist in two truncated forms of 140 amino acid and 139 amino acids in length. They differ from the full length form of the peptide by the proteolytic cleavage at amino acid residue number 14 (K) or amino acid residue 15 (F), respectively, $NH_2$-terminal amino acids (Gimenez-Gallego et al., 1986, Biochem. Biophys. Res. Comm. 138:611). The amino acid residue numbers relating to the truncated form of FGF-1 refer to the amino acid position relative to SEQ ID NO:2.

Figure 2:
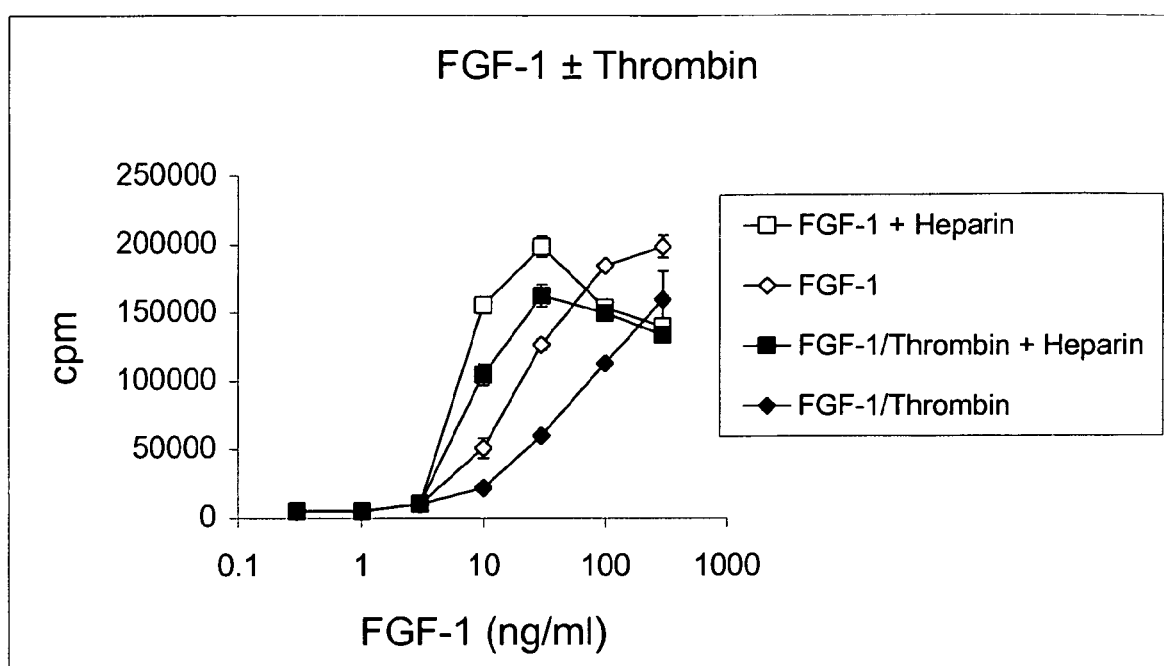

FIG. 2 is a graph depicting the effects of thrombin pretreatment on the ability of wild-type FGF-1 to induce proliferation of NIH 3T3 cells. NIH 3T3 cells were subjected to serum-starvation for 30 hours and the were grown in growth stimulation medium containing 1% bovine serum albumin, with or without heparin at 5 U/ml, and FGF-1 at the indicated concentrations. In some groups, FGF-1 was pretreated with thrombin at 10 U/ml for 24 hours. The cells were stimulated for 18 hours and then were pulsed with [$^3$H]-thymidine at 0.5 $\mu$Ci/ml for 6 hours. The ordinate represents [$^3$H]-thymidine incorporation into DNA, a measure of cell proliferation, expressed as counts per minute (cpm), and the abscissa represents the amount of FGF-1 used, expressed as ng/ml.

Figure 3:
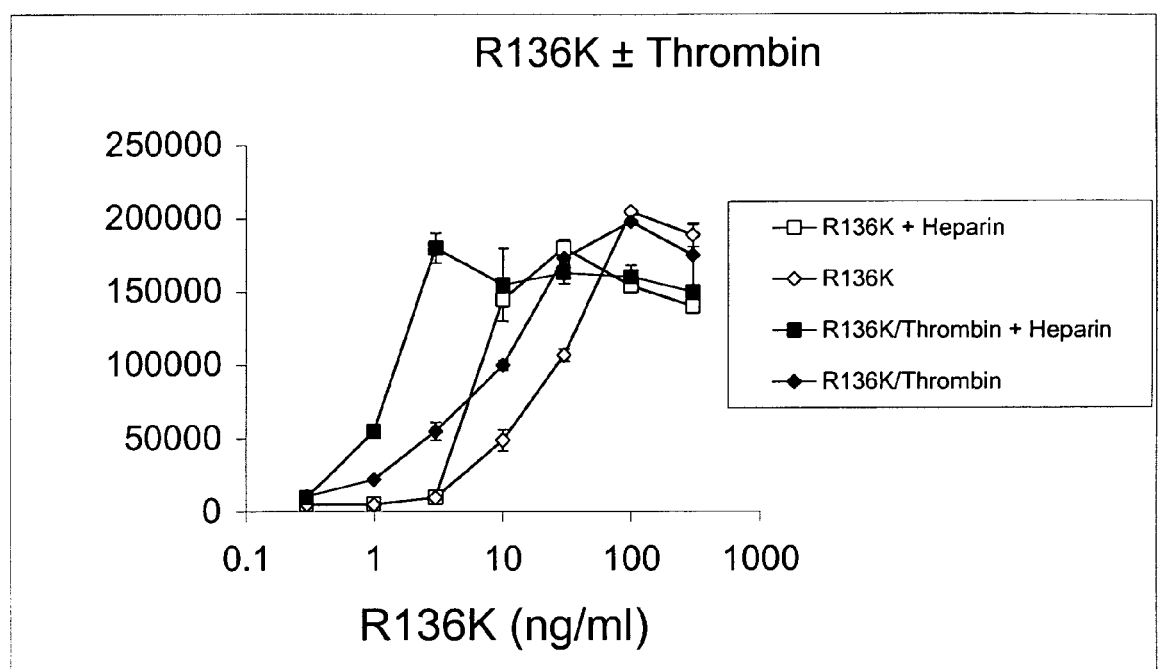

FIG. 3 is a graph depicting the ability of the thrombin-pretreated FGF-1 mutant, FGF-$1_{R136K}$, to induce proliferation of murine NIH 3T3 cells. NIH 3T3 cells were subjected to serum-starvation for 30 hours and then were grown in stimulation medium comprising 1% bovine serum albumin, with or without heparin at 10 $\mu$g/ml, and FGF-$1_{R136K}$ at the indicated concentrations. In the indicated groups, FGF-$1_{R136K}$ was pretreated with thrombin at 10 U/ml for 24 hours (closed squares and diamonds). The cells were stimulated for 18 hours and then were pulsed with [$^3$H]-thymidine at 0.5 $\mu$Ci/ml for 6 hours. The ordinate represents [$^3$H]-thymidine incorporation, expressed as counts per minute (cpm), and the abscissa represents the amount of FGF-$1_{R136K}$ used, expressed as ng/ml.

Figure 4:
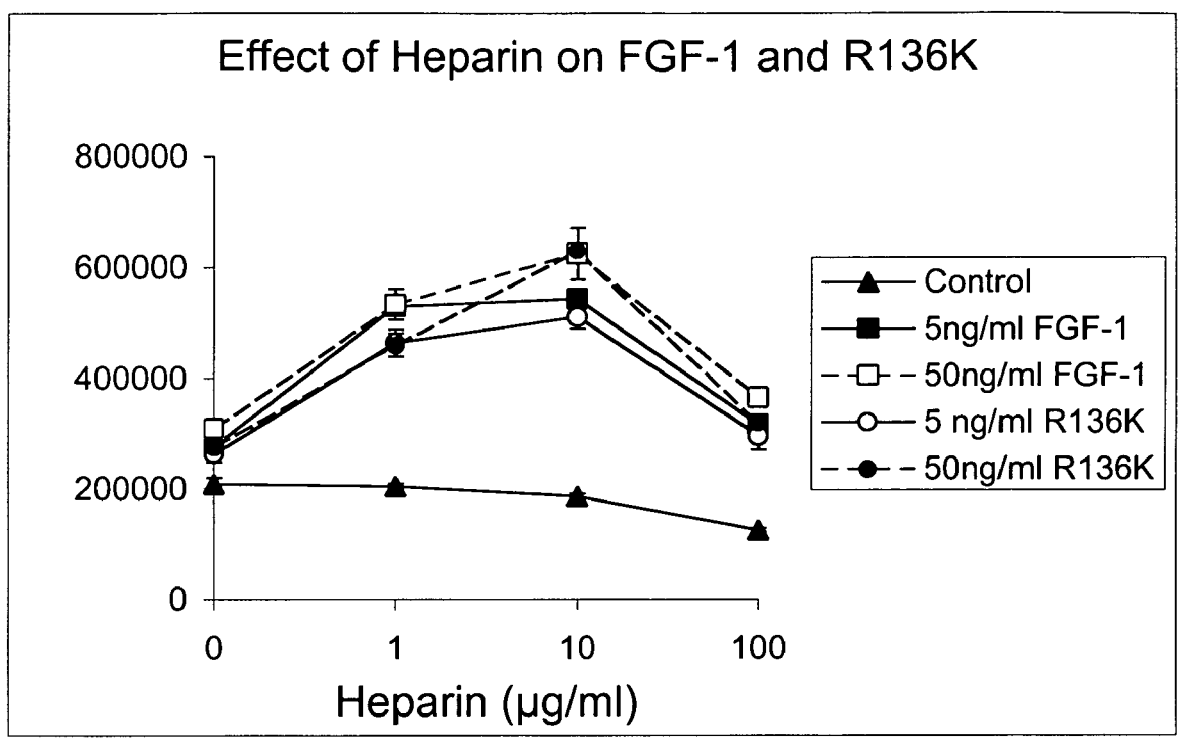

FIG. 4 is a graph demonstrating the effect of heparin on the biological activity of wild-type FGF-1 and on the FGF-1 mutant FGF-$1_{R136K}$, as determined by the effects of the growth factors on cell proliferation. Bovine aortic endothelial cells (BAEC) were plated at 20,000 cells/well in growth medium. Following attachment, the cells were grown in starvation medium and serum-starved for 24 hours. The cells were then grown in growth stimulation medium comprising various amounts of wild-type FGF-1, FGF-1$_{R136K}$, and heparin (0, 1, 10, and 100 µg/ml of heparin). More specifically, cells were grown in media comprising: 5 ng/ml wt FGF-1 (closed squares), 50 ng/ml wt FGF-1 (open squares), 5 ng/ml FGF-1$_{R136K}$ (open circles), or 50 ng/ml FGF-1$_{R136K}$ (closed circles). Following 3 days of stimulation, the BAECs were trypsinized and counted using a Coulter cell counter. Each point represents the average of three wells of a tissue culture plate. The ordinate represents the number of cells/well and the abscissa represents the concentration of heparin ([g/ml]) used.

Figure 5:
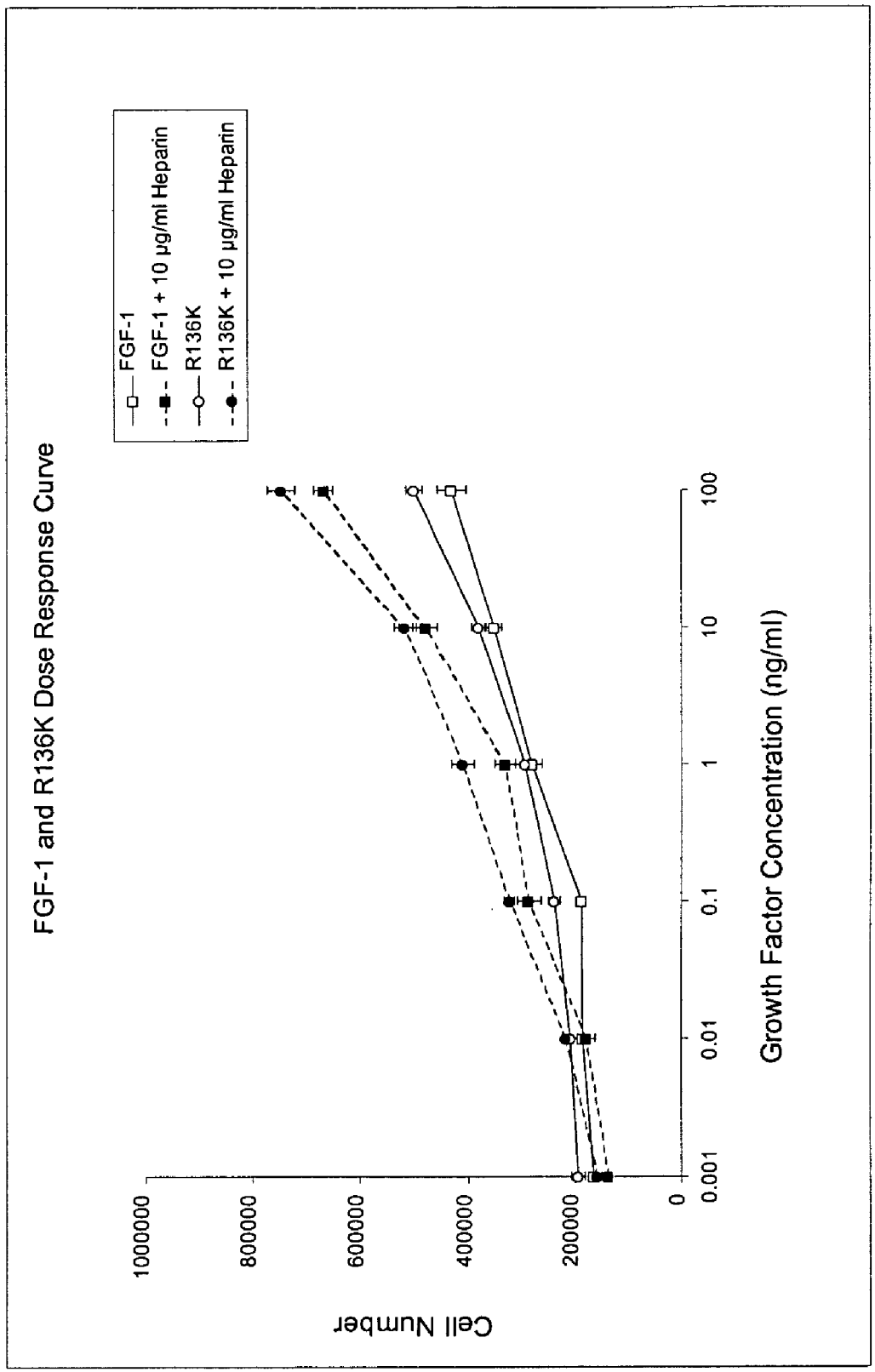

FIG. 5 is a graph depicting the biological activities of FGF-1 and FGF-1$_{R136K}$. Serum-starved bovine aortic endothelial cells (BAECs) were grown in growth medium comprising various amounts of FGF-1 or FGF-1$_{R136K}$, in the absence or presence of 10 µg/ml heparin. That is, the cells were grown in medium comprising: wt FGF-1 without heparin (open squares), wt FGF-1 and 10 µg/ml heparin (closed squares), FGF-1$_{R136K}$ (open circles), FGF-1$_{R136K}$ and 10 µg/ml heparin (closed circles). The ordinate represents the mean number of cells/well (measured in triplicate) three days after stimulation and the abscissa represents the concentration (ng/ml) of growth factor used.

Figure 6:
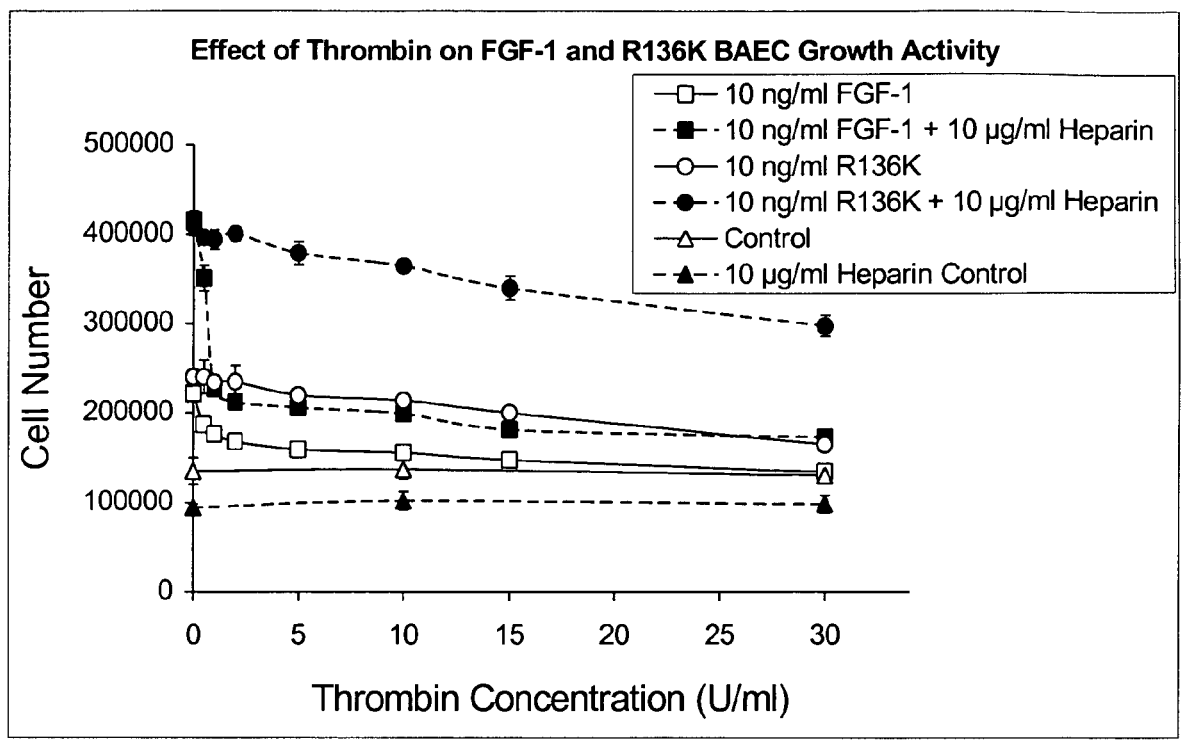

FIG. 6 is a graph illustrating the effect of thrombin pretreatment on the biological activity of FGF-1 and of FGF-1$_{R136K}$, as measured by bovine aortic endothelial cell (BAEC) growth. FGF-1 and FGF-1$_{R136K}$ were separately preincubated with various indicated amounts of thrombin in the absence or presence of 10 µg/ml heparin. After a 2 hour incubation, thrombin was inactivated by the addition of hirudin. The treated growth factors were then added at 10 ng/ml to the BAECs, which were counted 3 days later. The ordinate represents cell number (cells/well) and the abscissa represents thrombin concentration (U/ml).

Figure 7:
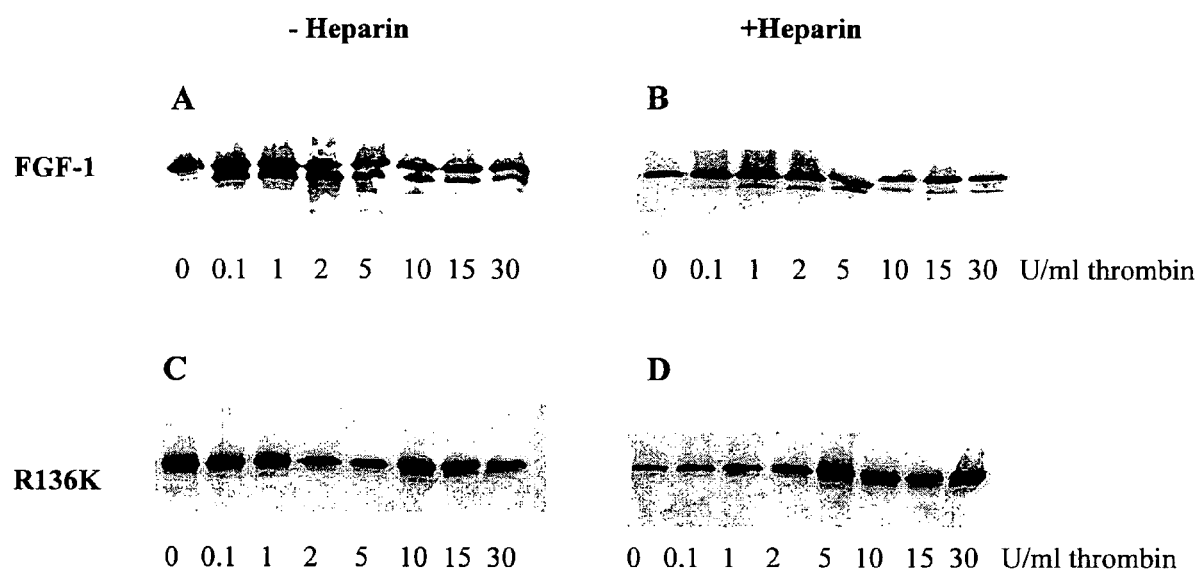

FIG. 7, comprising FIG. 7A, FIG. 7B, FIG. 7C, and FIG. 7D, is an image depicting Western blot analyses demonstrating the effects of thrombin incubation on growth factors wt FGF-1 and FGF-1$_{R136K}$ integrity. The growth factors were incubated for 2 hours at 37° C. with thrombin in the absence or presence of heparin. The growth factors were then subjected to SDS-PAGE, followed by transfer to PVDF membranes. The membranes were then immunostained for FGF-1 using antibodies that recognize both wt FGF-1 and FGF-1$_{R136K}$ and the immunoreactive protein bands were visualized using chemiluminescence. FIG. 7A depicts an image demonstrating degradation of wt FGF-1 incubated in various concentrations of thrombin in the absence of heparin. FIG. 7B depicts an image of a Western blot demonstrating proteolysis of wt FGF-1, which was incubated in various concentrations of thrombin while in the presence of heparin. FIG. 7C depicts an image of a Western blot demonstrating the effect of thrombin on mutant protein FGF-1$_{R136K}$ incubated with thrombin in the absence of heparin. FIG. 7D is an image of a Western blot demonstrating the effect of thrombin on mutant FGF-1$_{R136K}$ incubated with thrombin in the presence of heparin.

FIG. 8 depicts the nucleic acid sequence of wild type human FGF-1 (SEQ ID NO:1).

FIG. 9 depicts the amino acid sequence of wild type human FGF-1 (SEQ ID NO:2).

FIG. 10 sets forth the nucleic acid sequence of thrombin resistant mutant FGF-1$_{R136K}$ (SEQ ID NO:3).

FIG. 11 sets forth the amino acid sequence of thrombin resistant mutant FGF-1$_{R136K}$ (SEQ ID NO:4).

DETAILED DESCRIPTION OF THE INVENTION

The invention relates to a novel nucleic acid encoding a mutant FGF-1, a protein encoded thereby, and methods of using such molecules to treat diseases or disorders associated with, or mediated by, a process that is affected by contacting FGF-1 with a cell comprising an FGF-1 receptor. The invention relates to a mutant FGF-1 µl-§ wherein an amino acid substitution compared with the wild type amino acid sequence of FGF-1 protein surprisingly confers resistance to proteolysis and increases the biological activity of the mutant FGF-1 compared with wild type FGF-1 (wt FGF-1). More specifically, substitution of an arginine residue at position 136 of the wild type FGF-1 protein with a lysine residue produces a mutant FGF-1 (designated FGF-1$_{R136K}$) that is substantially resistant to thrombin cleavage and mediates a greater response in the presence of heparin, even in the absence of thrombin, when compared with wt FGF-1.

Increased resistance to thrombin inactivation has important implications in treatment of diseases or disorders that are otherwise treatable by administration of FGF-1 since the mutant FGF-1 is more stable and better able to reach the sites of FGF-1 action. This is because, as discussed previously elsewhere herein, degradation of FGF-1 by thrombin was a well-known limitation of prior art methods, which has been overcome by the present invention. Thus, the present invention overcomes a well-known obstacle in the prior art in that the mutant FGF-1 of the invention is resistant to thrombin inactivation and provides FGF-1 comprising enhanced ability to elicit FGF-1-mediated responses because, without wishing to be bound by any particular theory, more of the growth factor can reach the target and because it remains available longer before being degraded compared with wt FGF-1. Thus, the present invention has important implications in the development of therapeutics relating to use of FGF-1 for, inter alia, angiogenesis and repair, especially where thrombin degradation inhibits such processes.

Definitions

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

As used herein, amino acids are represented by the full name thereof, by the three letter code corresponding thereto, or by the one-letter code corresponding thereto, as indicated in the following table:

| Full Name | Three-Letter Code | One-Letter Code |
|---|---|---|
| Aspartic Acid | Asp | D |
| Glutamic Acid | Glu | E |
| Lysine | Lys | K |
| Arginine | Arg | R |
| Histidine | His | H |
| Tyrosine | Tyr | Y |
| Cysteine | Cys | C |
| Asparagine | Asn | N |
| Glutamine | Gln | Q |
| Serine | Ser | S |
| Threonine | Thr | T |
| Glycine | Gly | G |

-continued

| Full Name | Three-Letter Code | One-Letter Code |
|---|---|---|
| Alanine | Ala | A |
| Valine | Val | V |
| Leucine | Leu | L |
| Isoleucine | Ile | I |
| Methionine | Met | M |
| Proline | Pro | P |
| Phenylalanine | Phe | F |
| Tryptophan | Trp | W |

The term "antibody," as used herein, refers to an immunoglobulin molecule which is able to specifically bind to a specific epitope on an antigen. Antibodies can be intact immunoglobulins derived from natural sources or from recombinant sources and can be immunoreactive portions of intact immunoglobulins. Antibodies are typically tetramers of immunoglobulin molecules. The antibodies in the present invention may exist in a variety of forms including, for example, polyclonal antibodies, monoclonal antibodies, Fv, Fab and F(ab)$_2$, as well as single chain antibodies and humanized antibodies.

"Biological activity," or "biological function," as these terms are used herein means a biological response elicited or mediated by an FGF-1 molecule interacting with an FGF-1 receptor on a cell. Such response includes, but is not limited to, migration, proliferation, and differentiation of various cell types of mesodermal and neuroectodermal origins (e.g., endothelial cells, vascular smooth muscle cells, fibroblasts, epithelial cells, chondrocytes, osteoblasts oligiodendrocytes, and astrocytes,)s, and the like.

"Enhanced" or "extended" biological activity or function means that an FGF-1 molecule has a greater ability to elicit a biological response or that it has a greater half-life, or any such change that enhances, prolongs, or extends its function, compared with wild type FGF-1.

A "coding region" of a gene consists of the nucleotide residues of the coding strand of the gene and the nucleotides of the non-coding strand of the gene which are homologous with or complementary to, respectively, the coding region of an mRNA molecule which is produced by transcription of the gene.

"Complementary" as used herein refers to the broad concept of subunit sequence complementarity between two nucleic acids, e.g., two DNA molecules. When a nucleotide position in both of the molecules is occupied by nucleotides normally capable of base pairing with each other, then the nucleic acids are considered to be complementary to each other at this position. Thus, two nucleic acids are complementary to each other when a substantial number (at least 50%) of corresponding positions in each of the molecules are occupied by nucleotides which normally base pair with each other (e.g., A:T and G:C nucleotide pairs). Thus, it is known that an adenine residue of a first nucleic acid region is capable of forming specific hydrogen bonds ("base pairing") with a residue of a second nucleic acid region which is antiparallel to the first region if the residue is thymine or uracil. Similarly, it is known that a cytosine residue of a first nucleic acid strand is capable of base pairing with a residue of a second nucleic acid strand which is antiparallel to the first strand if the residue is guanine. A first region of a nucleic acid is complementary to a second region of the same or a different nucleic acid if, when the two regions are arranged in an antiparallel fashion, at least one nucleotide residue of the first region is capable of base pairing with a residue of the second region. Preferably, the first region comprises a first portion and the second region comprises a second portion, whereby, when the first and second portions are arranged in an antiparallel fashion, at least about 50%, and preferably at least about 75%, at least about 90%, or at least about 95% of the nucleotide residues of the first portion are capable of base pairing with nucleotide residues in the second portion. More preferably, all nucleotide residues of the first portion are capable of base pairing with nucleotide residues in the second portion. A "disease" is a state of health of an animal wherein the animal cannot maintain homeostasis, and wherein if the disease is not ameliorated then the animal's health continues to deteriorate.

As the term is used herein, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

An "effective amount" or an "effect dose" of a thrombin degradation resistant FGF-1, as used herein, refers to an amount of a thrombin degradation resistant FGF-1 which provides a detectable increase in an FGF-1 response and/or biological activity compared with an FGF-1 response before or in the absence of administration of resistant FGF-1. Preferably, the amount or dose provides a detectable increase in an FGF-1 response compared with the FGF-1 response mediated by an equal amount of a wild type FGF-1 that is not resistant to thrombin degradation.

A "therapeutically effective amount" is an amount of an FGF-1 which provides a therapeutic benefit, e.g., it treats or alleviates a disease or disorder, thereby providing a benefit to a mammal suffering from a disease or disorder that can be treated or alleviated by increasing the level of FGF-1 biological activity compared to the level of FGF-1 biological activity in the mammal prior to or in the absence of administration of FGF-1.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

"Fibroblast growth factors," or "FGFs," refers to a family of growth factors, which family includes FGF-1 and FGF-2, also known as acidic FGF and basic FGF, respectively. Although each member of the family shares certain characteristics with other members, each member also possesses some unique characteristics. The characteristics shared by these proteins include, but are not limited to the ability to bind heparin, bind to at least one of the four types of FGF cell surface receptors, ability to promote migration, proliferation and/or differentiation of various cell types.

As used here, "FGF-1 response," means any detectable change in a cell mediated by contacting the cell with an FGF-1, which change is mediated by the FGF-1 specifically binding with an FGF-1 receptor present on the cell surface, when compared with an otherwise identical cell not contacted with FGF-1. Such response includes, but is not limited to, increased incorporation of [$^3$H]thymidine into nascent DNA strands, cell proliferation, chemotaxis and migration, increased angiogenesis, increased nerve regeneration, injury repair, increase granulation tissue and increase rate of wound closure, and the like.

A disease or disorder "responsive to administration of FGF-1" is a disease or disorder that responds favorably to contacting a cell with an FGF-1 when compared to not contacting the cell with an FGF-1. Such disease or disorder includes, but is not limited to, myocardial ischemia, peripheral vascular disease, cerebral ischemia, epithelial injury, epidermal wound injury, nerve injury and bone damage.

"FGF treatable" is also used interchangeably with "FGF responsive" disease or disorder.

As used herein, the term "fragment" as applied to a nucleic acid, may be at least about 50 to about 100 nucleotides, more preferably, from about 100 to about 300 nucleotides, even more preferably, from about 300 to about 400 nucleotides, yet more preferably from about 400 to about 550 nucleotides, more preferably, from about 550 to about 580 nucleotides, and most preferably, from about 580 to about 600 nucleotides in length.

As applied to a protein, a "fragment" refers to a peptide of lesser length than the parental peptide. As used herein, a protein fragment is ordinarily at least about 50 contiguous amino acids, more preferably, about 50 to 100, even more preferably 100 to 139, most preferably, at least about 140 contiguous amino acids.

"Homologous" as used herein, refers to the subunit sequence similarity between two polymeric molecules, e.g., between two nucleic acid molecules, e.g., two DNA molecules or two RNA molecules, or between two polypeptide molecules. When a subunit position in both of the two molecules is occupied by the same monomeric subunit, e.g., if a position in each of two DNA molecules is occupied by adenine, then they are homologous at that position. The homology between two sequences is a direct function of the number of matching or homologous positions, e.g., if half (e.g., five positions in a polymer ten subunits in length) of the positions in two compound sequences are homologous then the two sequences are 50% homologous, if 90% of the positions, e.g., 9 of 10, are matched or homologous, the two sequences share 90% homology. By way of example, the DNA sequences 3'ATTGCC5' and 3'TATGGC share 50% homology.

As used herein, "homology" is used synonymously with "identity."

The determination of percent identity between two nucleotide or amino acid sequences can be accomplished using a mathematical algorithm. For example, a mathematical algorithm useful for comparing two sequences is the algorithm of Karlin and Altschul (1990, Proc. Natl. Acad. Sci. USA 87:2264–2268), modified as in Karlin and Altschul (1993, Proc. Natl. Acad. Sci. USA 90:5873–5877). This algorithm is incorporated into the NBLAST and XBLAST programs of Altschul, et al. (1990, J. Mol. Biol. 215:403–410), and can be accessed, for example at the National Center for Biotechnology Information (NCBI) world wide web site.

BLAST nucleotide searches can be performed with the NBLAST program (designated "blastn" at the NCBI web site), using the following parameters: gap penalty=5; gap extension penalty=2; mismatch penalty=3; match reward=1; expectation value 10.0; and word size=11 to obtain nucleotide sequences homologous to a nucleic acid described herein. BLAST protein searches can be performed with the XBLAST program (designated "blastn" at the NCBI web site) or the NCBI "blastp" program, using the following parameters: expectation value 10.0, BLOSUM62 scoring matrix to obtain amino acid sequences homologous to a protein molecule described herein. To obtain gapped alignments for comparison purposes, Gapped BLAST can be utilized as described in Altschul et al. (1997, Nucleic Acids Res. 25:3389–3402). Alternatively, PSI-Blast or PHI-Blast can be used to perform an iterated search which detects distant relationships between molecules (Id.) and relationships between molecules which share a common pattern. When utilizing BLAST, Gapped BLAST, PSI-Blast, and PHI-Blast programs, the default parameters of the respective programs (e.g., XBLAST and NBLAST) can be used.

The percent identity between two sequences can be determined using techniques similar to those described above, with or without allowing gaps. In calculating percent identity, typically exact matches are counted.

As used herein, an "instructional material" includes a publication, a recording, a diagram, or any other medium of expression which can be used to communicate the usefulness of the peptide of the invention in the kit for effecting alleviation of the various diseases or disorders recited herein. Optionally, or alternately, the instructional material may describe one or more methods of alleviating the diseases or disorders in a cell or a tissue of a mammal. The instructional material of the kit of the invention may, for example, be affixed to a container which contains the identified compound invention or be shipped together with a container which contains the identified compound. Alternatively, the instructional material may be shipped separately from the container with the intention that the instructional material and the compound be used cooperatively by the recipient.

An "isolated nucleic acid" refers to a nucleic acid segment or fragment which has been separated from sequences which flank it in a naturally occurring state, e.g., a DNA fragment which has been removed from the sequences which are normally adjacent to the fragment, e.g., the sequences adjacent to the fragment in a genome in which it naturally occurs. The term also applies to nucleic acids which have been substantially purified from other components which naturally accompany the nucleic acid, e.g., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (e.g, as a cDNA or a genomic or cDNA fragment produced by PCR or restriction enzyme digestion) independent of other sequences. It also includes a recombinant DNA which is part of a hybrid gene encoding additional polypeptide sequence.

A "ligand" is a compound that specifically binds with a target receptor.

A "receptor" is a compound that specifically binds to a ligand.

A molecule (e.g., a ligand, a receptor, an antibody, and the like) "specifically binds with" or "is specifically immunoreactive with" another molecule where it binds preferentially with the compound and does not bind in a significant amount to other compounds present in the sample.

By "nucleic acid" is meant any nucleic acid, whether composed of deoxyribonucleosides or ribonucleosides, and whether composed of phosphodiester linkages or modified linkages such as phosphotriester, phosphoramidate, siloxane, carbonate, carboxymethylester, acetamidate, carbamate, thioether, bridged phosphoramidate, bridged methylene phosphonate, bridged phosphoramidate, bridged phosphoramidate, bridged methylene phosphonate, phosphorothioate, methylphosphonate, phosphorodithioate, bridged phosphorothioate or sulfone linkages, and combinations of such linkages. The term nucleic acid also specifically includes nucleic acids composed of bases other than the five biologically occurring bases (adenine, guanine, thymine, cytosine and uracil).

The term "oligonucleotide" typically refers to short polynucleotides, generally, no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

The term "nucleic acid construct," as used herein, encompasses DNA and RNA sequences encoding the particular gene or gene fragment desired, whether obtained by genomic or synthetic methods.

By describing two polynucleotides as "operably linked" is meant that a single-stranded or double-stranded nucleic acid moiety comprises the two polynucleotides arranged within the nucleic acid moiety in such a manner that at least one of the two polynucleotides is able to exert a physiological effect by which it is characterized upon the other. By way of example, a promoter operably linked to the coding region of a gene is able to promote transcription of the coding region.

A "polynucleotide" means a single strand or parallel and anti-parallel strands of a nucleic acid. Thus, a polynucleotide may be either a single-stranded or a double-stranded nucleic acid.

"Primer" refers to a polynucleotide that is capable of specifically hybridizing to a designated polynucleotide template and providing a point of initiation for synthesis of a complementary polynucleotide. Such synthesis occurs when the polynucleotide primer is placed under conditions in which synthesis is induced, i.e., in the presence of nucleotides, a complementary polynucleotide template, and an agent for polymerization such as DNA polymerase. A primer is typically single-stranded, but may be double-stranded. Primers are typically deoxyribonucleic acids, but a wide variety of synthetic and naturally occurring primers are useful for many applications.

A primer is complementary to the template to which it is designed to hybridize to serve as a site for the initiation of synthesis, but need not reflect the exact sequence of the template. In such a case, specific hybridization of the primer to the template depends on the stringency of the hybridization conditions. Primers can be labeled with, e.g., chromogenic, radioactive, or fluorescent moieties and used as detectable moieties.

As used herein, the term "promoter/regulatory sequence" means a nucleic acid sequence which is required for expression of a gene product operably linked to the promoter/regulator sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

A "constitutive" promoter is a promoter which drives expression of a gene to which it is operably linked, in a constant manner in a cell. By way of example, promoters which drive expression of cellular housekeeping genes are considered to be constitutive promoters.

An "inducible" promoter is a nucleotide sequence which, when operably linked with a polynucleotide which encodes or specifies a gene product, causes the gene product to be produced in a living cell substantially only when an inducer which corresponds to the promoter is present in the cell.

A "tissue-specific" promoter is a nucleotide sequence which, when operably linked with a polynucleotide which encodes or specifies a gene product, causes the gene product to be produced in a living cell substantially only if the cell is a cell of the tissue type corresponding to the promoter.

The term "protein" typically refers to large polypeptides.
The term "peptide" typically refers to short polypeptides.

"Polypeptide" refers to a polymer composed of amino acid residues, related naturally occurring structural variants, and synthetic non-naturally occurring analogs thereof linked via peptide bonds, related naturally occurring structural variants, and synthetic non-naturally occurring analogs thereof.

An "isolated polypeptide" refers to a polypeptide which has been substantially purified from other peptides or molecules which naturally accompany it in a cell or which are present following a modification or purification procedure. A compound, e.g., a protein or polypeptide, is also substantially purified when it is essentially free of naturally associated components or when it is separated from the native contaminants which accompany it in its natural state.

"Synthetic peptides or polypeptides" means a non-naturally occurring peptide or polypeptide. Synthetic peptides or polypeptides can be synthesized, for example, using an automated polypeptide synthesizer. Various solid phase peptide synthesis methods are known to those of skill in the art.

"Recombinant polynucleotide" refers to a polynucleotide having sequences that are not naturally joined together. An amplified or assembled recombinant polynucleotide may be included in a suitable vector, and the vector can be used to transform a suitable host cell.

A recombinant polynucleotide may serve a non-coding function (e.g., promoter, origin of replication, ribosome-binding site, etc.) as well.

A host cell that comprises a recombinant polynucleotide is referred to as a "recombinant host cell." A gene which is expressed in a recombinant host cell wherein the gene comprises a recombinant polynucleotide, produces a "recombinant polypeptide."

A "recombinant polypeptide" is one which is produced upon expression of a recombinant polynucleotide.

A "recombinant cell" is a cell that comprises a transgene. Such a cell may be a eukaryotic or a prokaryotic cell. Also, the transgenic cell encompasses, but is not limited to, an embryonic stem cell comprising the transgene, a cell obtained from a chimeric mammal derived from a transgenic embryonic stem cell where the cell comprises the transgene, a cell obtained from a transgenic mammal, or fetal or placental tissue thereof, and a prokaryotic cell comprising the transgene.

As used herein, the term "reporter gene" means a gene, the expression of which can be detected using a known method. By way of example, the *Escherichia coli* lacZ gene may be used as a reporter gene in a medium because expression of the lacZ gene can be detected using known methods by adding the chromogenic substrate o-nitrophenyl-β-galactoside to the medium (Gerhardt et al., eds., 1994, In: Methods for General and Molecular Bacteriology, p. 574, American Society for Microbiology, Washington, D.C.).

By "tag" polypeptide is meant any protein which, when linked by a peptide bond to a protein of interest, may be used to localize the protein, to purify it from a cell extract, to immobilize it for use in binding assays, or to otherwise study its biological properties and/or function.

As used herein, the term "transgene" means an exogenous nucleic acid sequence which exogenous nucleic acid is encoded by a transgenic cell or mammal.

As used herein, the term "transgenic mammal" means a mammal, the germ cells of which comprise an exogenous nucleic acid.

The term to "treat," as used herein, means reducing the frequency with which symptoms are experienced by a patient or subject or administering an agent or compound to reduce the frequency with which symptoms are experienced.

As used herein, "alleviating" a disease or disorder symptom means reducing the severity of a symptom of the disease or disorder.

As used herein, "treating a fibroblast growth factor treatable disease or disorder" means reducing the frequency with which a symptom of the viral disease or disorder is experienced by a patient. Fibroblast growth factor treatable disease or disorder is used interchangeably herein with FGF-treatable disease or disorder.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer or delivery of nucleic acid to cells, such as, for example, polylysine compounds, liposomes, and the like. Examples of viral vectors include, but are not limited to, adenoviral vectors, adeno-associated virus vectors, retroviral vectors, recombinant viral vectors, and the like. Examples of non-viral vectors include, but are not limited to, liposomes, polyamine derivatives of DNA and the like.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses that incorporate the recombinant polynucleotide.

"Wild-type," as used herein refers to a native molecule, or to the parental molecule from which a mutant, fragment, or derivative is derived. Preferably, wild type FGF-1 comprises the amino acid sequence of SEQ ID NO:2 and/or is encoded by a nucleic acid comprising the nucleic acid sequence of SEQ ID NO: 1. Preferably, wild type FGF-1 does not comprise a lysine residue at amino acid residue number 136, more preferably, wild type FGF-1 comprises an arginine residue at amino acid number 136, relative to the sequence of SEQ ID NO:2. Most preferably, wild type FGF-1 has the amino acid sequence of SEQ ID NO:2 and/or is encoded by a nucleic acid having the sequence of SEQ ID NO: 1.

"Mutant FGF-1", as used herein, refers to an FGF-1 molecule that is resistant to thrombin degradation when compared to wild type FGF-1 treated under otherwise identical conditions. That is, the FGF-1 retains a detectably higher level of activity when treated with thrombin when compared with wild type FGF-1 treated under essentially identical conditions. Preferably, mutant thrombin resistant FGF-1 comprises an amino acid residue at position number 136 that is not arginine, relative to SEQ ID NO:2. More preferably, the mutant or thrombin resistant FGF-1 comprises a lysine residue at amino acid number 136. Most preferably, a mutant thrombin resistant FGF-1 has the sequence of SEQ ID NO:4.

DESCRIPTION

I. Isolated nucleic acids

The present invention includes an isolated nucleic acid encoding a mutant FGF-1, wherein the nucleic acid sequence of the nucleic acid comprises the sequence of SEQ ID NO:3. Further, one skilled in the art would appreciate, based upon the disclosure provided herein, that the invention encompasses an isolated nucleic acid encoding a thrombin degradation resistant FGF-1 wherein the triplet at nucleotides 443–445 relative to SEQ ID NO: 1 are AAA or AAG, since these triplets encode the amino acid residue lysine. This is because, as disclosed elsewhere herein, substitution of the triplet CGG, which specifies arginine, with the triplet AAA, specifying lysine, results in an FGF-1 polypeptide that demonstrates thrombin degradation resistance. Therefore, the skilled artisan would appreciate, armed with the teachings provided herein, that any triplet specifying lysine can be substituted at nucleotides 443–445 to produce a thrombin degradation resistant FGF-1.

Further, one skilled in the art would understand, based upon the disclosure provided herein, that the invention includes an isolated nucleic acid encoding a thrombin degradation resistant FGF-1 wherein the nucleic acid comprises the sequence of SEQ ID NO: 1 but where the nucleotides at positions 443–445 are not CGG, CGT, CGC, CGA, AGA, or AGG. This is because these aforementioned triplets all encode arginine, which when present in the amino acid sequence at position number 136 relative to SEQ ID NO:2, renders the polypeptide encoded by the nucleic acid sensitive to thrombin cleavage. Therefore, the skilled artisan would appreciate, based upon the teachings provided herein, that a nucleic acid that does not encode an arginine residue at amino acid position 136 relative to SEQ ID NO:2, can encode a thrombin degradation resistant FGF-1 of the invention.

In another aspect, the present invention includes an isolated nucleic acid encoding a mutant FGF-1, or a fragment thereof, wherein the protein encoded by the nucleic acid has the protein sequence of SEQ ID NO:4.

The isolated nucleic acid of the invention should be construed to include an RNA or a DNA sequence encoding a FGF-1 protein of the invention, and any modified forms thereof, including chemical modifications of the DNA or RNA which render the nucleotide sequence more stable when it is cell free or when it is associated with a cell. Chemical modifications of nucleotides may also be used to enhance the efficiency with which a nucleotide sequence is taken up by a cell or the efficiency with which it is expressed in a cell. Any and all combinations of modifications of the nucleotide sequences are contemplated in the present invention.

The present invention should not be construed as being limited solely to the nucleic and amino acid sequences disclosed herein. Once armed with the present invention, one skilled in the art could produce nucleic acids encoding thrombin resistant FGF-1 proteins by following the procedures described herein in the experimental details section for the isolation of human nucleic acids encoding thrombin resistant FGF-1 polypeptides (e.g., screening of genomic or cDNA libraries), and procedures that are well-known in the art (e.g., reverse transcription PCR using mRNA samples and antibody-based methods), or to be developed.

Further, any number of procedures can be used for the generation of mutant, derivative or variant forms of FGF-1 using recombinant DNA methodology well known in the art such as, for example, that described in Sambrook et al. (1989, In: Molecular Cloning: A Laboratory Manual, Cold Spring Harbor Laboratory Press, New York) and Ausubel et al. (1997, Current Protocols in Molecular Biology, Green & Wiley, New York), and as set forth elsewhere herein.

Procedures for the introduction of amino acid changes in a protein or polypeptide by altering the DNA sequence encoding the polypeptide are disclosed herein, are well known in the art, and are also described in Sambrook et al. (1989, supra); Ausubel et al. (1997, supra).

The invention includes a nucleic acid encoding a mutant FGF-1 wherein the nucleic acid encoding a tag polypeptide is covalently linked thereto. That is, the invention encompasses a chimeric nucleic acid wherein the nucleic acid sequences encoding a tag polypeptide is covalently linked to the nucleic acid encoding human mutant FGF-1. Such tag polypeptides are well known in the art and include, for instance, green fluorescent protein, myc, myc-pyruvate kinase (myc-PK), $His_6$, maltose biding protein (MBP), an influenza virus hemagglutinin tag polypeptide, a flag tag polypeptide, and a glutathione-S-transferase (GST) tag polypeptide. However, the invention should in no way be construed to be limited to the nucleic acids encoding the above-listed tag polypeptides. Rather, any nucleic acid sequence encoding a polypeptide which may function in a manner substantially similar to these tag polypeptides should be construed to be included in the present invention.

The nucleic acid comprising a nucleic acid encoding a tag polypeptide can be used to localize mutant FGF-1 within a cell, a tissue, and/or a whole organism (e.g., a mammalian embryo), detect mutant FGF-1 secreted from a cell, and to study the role(s) of mutant FGF-1 in a cell. Further, addition of a tag polypeptide facilitates isolation and purification of the "tagged" protein such that the proteins of the invention can be produced and purified readily.

II. Isolated polypeptides

The invention also includes an isolated polypeptide comprising a mutant FGF-1 molecule. Preferably, the isolated polypeptide has the sequence of SEQ ID NO:4.

One skilled in the art, armed with the teachings provided herein, would appreciate that other variants of FGF-1 can be produced that can resist thrombin degradation relative to wt FGF-1, which comprise a lysine at amino acid residue number 136. That is, the invention includes thrombin resistant FGF-1 polypeptides comprising the amino acid sequence of SEQ ID NO:2, except the amino acid residue at position number 136 is lysine. Thus, the sequence of thrombin resistant FGF-1 encompasses variants of wt FGF-1 wherein the amino acid at position 136 is lysine. Thrombin resistant variants comprising a lysine at amino acid residue number 136 relative to SEQ ID NO:4 can be readily assessed for thrombin degradation resistance using a wide plethora of assays disclosed herein, well-known in the art, or developed in the future, and such assays are not therefore enumerated herein.

Further, one skilled in the art would appreciate, based upon the disclosure provided herein, that the invention encompasses a mutant FGF-1 polypeptide where the amino acid residue at position number 136 relative to SEQ ID NO:2 is not arginine. More preferably, the amino acid residue at position number 136 is lysine. Most preferably, the mutant FGF-1 has the amino acid sequence of SEQ ID NO:4. This is because the data disclosed herein demonstrate that even a conservative substitution of the arginine residue at position number 136 with lysine, rendered the FGF-1 resistant to thrombin degradation relative to wild type FGF-1. Thus, the skilled artisan would understand, based upon the disclosure provided herein, that other amino acid substitutions, including the even more drastic non-conservative substitutions, can also confer resistance to thrombin degradation. Thus, it would be understood, given the teachings provided herein, that the skilled artisan can readily identify a mutant FGF-1 resistant to thrombin degradation in that the routineer can introduce other amino acid substitutions at amino acid residue number 136 and assess the mutant FGF-1 produced for thrombin degradation resistance using the assays and methods disclosed elsewhere herein, or using assays and methods well-known in the art or to be developed in the future.

In addition to the full length FGF-1 mutant (i.e., a protein comprising about 154 amino acid residues), one skilled in the art would understand that the invention includes a mutant FGF-1 resistant to thrombin degradation wherein about 14 or 15 N-terminal amino acid residues are not present. That is, the invention includes two truncated forms of FGF-1 (i.e., a truncated form comprising from about amino acid residue number 14 to amino acid residue number 154 and a truncated form comprising from about amino acid 15 to amino acid residue 154) that can also be mutated to produce a thrombin-resistant mutant FGF-1.

The present invention also provides for analogs of proteins or peptides which comprise a mutant FGF-1 as disclosed herein. Analogs may differ from naturally occurring proteins or peptides by conservative amino acid sequence differences or by modifications which do not affect sequence, or by both. For example, conservative amino acid changes may be made, which although they alter the primary sequence of the protein or peptide, do not normally alter its function. Conservative amino acid substitutions typically include substitutions within the following groups:

glycine, alanine;
valine, isoleucine, leucine;
aspartic acid, glutamic acid;
asparagine, glutamine;
serine, threonine;
lysine, arginine;
phenylalanine, tyrosine.

Modifications (which do not normally alter primary sequence) include in vivo, or in vitro, chemical derivatization of polypeptides, e.g., acetylation, or carboxylation. Also included are modifications of glycosylation, e.g., those made by modifying the glycosylation patterns of a polypeptide during its synthesis and processing or in further processing steps; e.g., by exposing the polypeptide to enzymes which affect glycosylation, e.g., mammalian glycosylating or deglycosylating enzymes. Also embraced are sequences which have phosphorylated amino acid residues, e.g., phosphotyrosine, phosphoserine, or phosphothreonine.

Also included are polypeptides which have been modified using ordinary molecular biological techniques so as to improve their resistance to proteolytic degradation or to optimize solubility properties or to render them more suitable as a therapeutic agent. Analogs of such polypeptides include those containing residues other than naturally occurring L-amino acids, e.g., D-amino acids or non-naturally occurring synthetic amino acids. The peptides of the invention are not limited to products of any of the specific exemplary processes listed herein.

The present invention should also be construed to encompass "mutants," "derivatives," and "variants" of the peptides of the invention (or of the DNA encoding the same) which mutants, derivatives and variants are FGF-1 peptides which are altered in one or more amino acids (or, when referring to the nucleotide sequence encoding the same, are altered in one or more base pairs) such that the resulting peptide (or DNA) is not identical to the sequences recited herein, but has the same biological property as the peptides disclosed herein, in that the peptide has biological/biochemical properties of the thrombin resistant FGF-1 peptide of the present invention.

A biological property of a thrombin resistant FGF-1 protein should be construed but not be limited to include, the ability to specifically bind with an FGF-1 receptor, the ability to resist degradation by thrombin compared with wild type FGF-1, the ability to bind to heparin to increase FGF-1 stability and biological activity, the ability to bind to heparan sulfate to increase FGF-1 stability and biological activity, the ability to bind to fibrinogen, the ability to bind to fibrin, and the like.

The nucleic acids, and peptides encoded thereby, are useful tools to produce recombinant cells and transgenic non-human mammals, which are useful tools for the study of thrombin resistant FGF-1 action, the identification of novel therapeutics for repair of vascular and nerve injury, promotion of angiogenesis, cell proliferation, and for elucidating the cellular role(s) of FGF-1, among other things.

III. Vectors

In other related aspects, the invention includes an isolated nucleic acid encoding a thrombin resistant FGF-1 operably linked to a nucleic acid comprising a promoter/regulatory sequence such that the nucleic acid is preferably capable of directing expression of the protein encoded by the nucleic acid. Thus, the invention encompasses expression vectors and methods for the introduction of exogenous DNA into cells with concomitant expression of the exogenous DNA in the cells such as those described, for example, in Sambrook et al. (1989, supra), and Ausubel et al. (1997, supra).

Expression of thrombin resistant FGF-1 in cells which either do not normally express thrombin resistant FGF-1, or which do not express such FGF-1 constructs fused with a tag polypeptide, can be accomplished by generating a plasmid, viral, or other type of vector comprising the desired nucleic acid operably linked to a promoter/regulatory sequence which serves to drive expression of the protein, with or without tag, in cells in which the vector is introduced.

Many promoter/regulatory sequences useful for driving constitutive expression of a gene are available in the art and include, but are not limited to, for example, the adenovirus (ADV), the cytomegalovirus (CMV) immediate early promoter enhancer sequence, the SV40 early promoter, both of which were used in the experiments disclosed herein, as well as the Rous sarcoma virus promoter, and the like. Moreover, inducible and tissue specific expression of the nucleic acid encoding thrombin resistant FGF-1 can be accomplished by placing the nucleic acid encoding thrombin resistant FGF-1, with or without a tag, under the control of an inducible or tissue specific promoter/regulatory sequence. Examples of tissue specific or inducible promoter/regulatory sequences which are useful for his purpose include, but are not limited to the MMTV LTR inducible promoter, and the SV40 late enhancer/promoter. In addition, promoters which are well known in the art which are induced in response to inducing agents such as metals, glucocorticoids, and the like, are also contemplated in the invention. Thus, it will be appreciated that the invention includes the use of any promoter/regulatory sequence, which is either known or unknown, and which is capable of driving expression of the desired protein operably linked thereto.

Expressing thrombin resistant FGF-1 using a vector allows the isolation of large amounts of recombinantly produced protein. Further, where the lack or decreased level of thrombin resistant FGF-1 expression causes a disease, disorder, or condition associated with such expression, the expression of thrombin resistant FGF-1 driven by a promoter/regulatory sequence can provide useful therapeutics including, but not limited to, gene therapy whereby thrombin resistant FGF-1 is provided and or administration of thrombin resistant FGF-1 by administering the nucleic acid from which it is then expressed. A disease, disorder or condition associated with a decreased level of expression, level of protein, or decreased activity of the protein, and/or for which administration of thrombin resistant FGF-1 can be useful includes, but is not limited to, myocardial ischemia, peripheral vascular disease, cerebral ischemia, epithelial injury, epidermal wound injury, nerve injury, and bone damage, and the like. Therefore, the invention includes not only methods of inhibiting thrombin resistant FGF-1 expression, translation, and/or activity, but it also includes methods relating to increasing thrombin resistant FGF-1 expression, protein level, and/or activity since both decreasing and increasing thrombin resistant FGF-1 expression and/or activity can be useful in providing effective therapeutics.

Selection of any particular plasmid vector or other DNA vector is not a limiting factor in this invention and a wide plethora vectors is well-known in the art. Further, it is well within the skill of the artisan to choose particular promoter/regulatory sequences and to operably link those promoter/regulatory sequences to a DNA sequence encoding a desired polypeptide. Such technology is well known in the art and is described, for example, in Sambrook et al. (1989, In: Molecular Cloning: A Laboratory Manual, Cold Spring Harbor Laboratory Press, New York) and Ausubel et al. (1997, Current Protocols in Molecular Biology, Green & Wiley, New York).

The invention thus includes a vector comprising an isolated nucleic acid encoding a mammalian thrombin resistant FGF-1. The incorporation of a desired nucleic acid into a vector and the choice of vectors is well-known in the art as described in, for example, Sambrook et al., supra, and Ausubel et al., supra.

The invention also includes cells, viruses, proviruses, and the like, containing such vectors. Methods for producing cells comprising vectors and/or exogenous nucleic acids are well-known in the art. See, e.g., Sambrook et al., supra; Ausubel et al., supra.

The nucleic acids encoding thrombin resistant FGF-1 may be cloned into various plasmid vectors. However, the present invention should not be construed to be limited to plasmids or to any particular vector. Instead, the present invention should be construed to encompass a wide plethora of vectors which are readily available and/or well-known in the art.

IV. Recombinant cells and transgenic non-human mammals

The invention includes a recombinant cell comprising, inter alia, an isolated nucleic acid encoding thrombin resistant FGF-1. In one aspect, the recombinant cell can be transiently transfected with a plasmid encoding a portion of the nucleic acid encoding thrombin resistant FGF-1. The nucleic acid need not be integrated into the cell genome nor does it need to be expressed in the cell. Moreover, the cell may be a prokaryotic or a eukaryotic cell and the invention should not be construed to be limited to any particular cell line or cell type. Such cells include, but are not limited to, bacterial cells such as *Escherichia coli*, endothelial cells, vascular smooth muscle cells, fibroblasts, epithelial cells, chondrocytes, osteoblasts oligiodendrocytes, and astrocytes.

In one aspect, the recombinant cell comprising an isolated nucleic acid encoding thrombin resistant FGF-1 is used to produce a transgenic non-human mammal. That is, the exogenous nucleic acid, or transgene as it is also referred to herein, of the invention is introduced into a cell, and the cell is then used to generate the non-human transgenic mammal. The cell into which the transgene is introduced is preferably an embryonic stem (ES) cell. However, the invention should not be construed to be limited solely to ES cells comprising the transgene of the invention nor to cells used to produce transgenic animals. Rather, a transgenic cell of the invention includes, but is not limited to, any cell derived from a transgenic animal comprising a transgene, a cell comprising the transgene derived from a chimeric animal derived from the transgenic ES cell, and any other comprising the transgene which may or may not be used to generate a non-human transgenic mammal.

Further, it is important to note that the purpose of transgene-comprising, i.e., recombinant, cells should not be construed to be limited to the generation of transgenic mammals. Rather, the invention should be construed to include any cell type into which a nucleic acid encoding a thrombin resistant FGF-1 is introduced, including, without limitation, a prokaryotic cell and a eukaryotic cell comprising an isolated nucleic acid encoding thrombin resistant FGF-1.

The invention includes a eukaryotic cell which, when the transgene of the invention is introduced therein, and the protein encoded by the desired gene is expressed therefrom where it was not previously present or expressed in the cell or where it is now expressed at a level or under circumstances different than that before the transgene was introduced, a benefit is obtained. Such a benefit may include the fact that there has been provided a system in the expression of the desired gene, i.e., thrombin resistant FGF-1, can be studied in vitro in the laboratory or in a mammal in which the cell resides, a system wherein cells comprising the introduced gene can be used as research, diagnostic and therapeutic tools, and a system wherein animal models are generated which are useful for the development of new diagnostic and therapeutic tools for selected disease states in a mammal.

Such cell expressing an isolated nucleic acid encoding thrombin resistant FGF-1 can be used to provide thrombin resistant FGF-1 to a cell, tissue, or whole animal where expression of thrombin resistant FGF-1 can be useful to treat or alleviate a disease, disorder or condition associated with or worsened by thrombin degradation FGF-1 and/or such diseases or disorders that would be alleviated or treated by administration of FGF-1 to a cell or tissue but wherein such administration is otherwise impeded or inhibited by degradation of FGF-1 by thrombin. Such diseases, disorders or conditions can include, but are not limited to myocardial ischemia, peripheral vascular disease, cerebral ischemia, epithelial injury, epidermal wound injury, nerve injury, and bone damage, and the like. Therefore, the invention includes a cell expressing thrombin resistant FGF-1 to increase or induce thrombin resistant FGF-1 expression, translation, and/or activity, where increasing thrombin resistant FGF-1 expression, protein level, and/or activity can be useful to treat or alleviate a disease, disorder or condition.

One of ordinary skill would appreciate, based upon the disclosure provided herein, that a "knock-in" vector of the invention comprises at least two sequences homologous to two portions of the nucleic acid which is to be replaced. The two sequences are homologous with sequences that flank the gene; that is, one sequence is homologous with a region at or near the 5' portion of the coding sequence of the nucleic acid encoding thrombin resistant FGF-1 and the other sequence is further downstream from the first. One skilled in the art would appreciate, based upon the disclosure provided herein, that the present invention is not limited to any specific flanking nucleic acid sequences. Instead, the targeting vector may comprise two sequences which insert (i.e., a "knock-in" vector) a nucleic acid encoding thrombin resistant FGF-1, or a fragment thereof, into a mammalian genome. The crucial feature of the targeting vector is that it comprise sufficient portions of two sequences located towards opposite, i.e., 5' and 3', ends of the thrombin resistant FGF-1 open reading frame (ORF), to allow insertion by homologous recombination to occur such that all or a portion of the nucleic acid encoding thrombin resistant FGF-1 is inserted into a location on a mammalian chromosome.

The design of transgenes and knock-in targeting vectors is well-known in the art and is described in standard treatises such as Sambrook et al. (1989, Molecular Cloning: A Laboratory Manual, Cold Spring Harbor Laboratory, New York), and in Ausubel et al. (1997, Current Protocols in Molecular Biology, John Wiley & Sons, New York), and the like. The upstream and downstream portions flanking or within the thrombin resistant FGF-1 coding region to be used in the targeting vector may be easily selected based upon known methods and following the teachings disclosed herein based on the disclosure provided herein including the nucleic and amino acid sequences of human thrombin resistant FGF-1. Armed with these sequences, one of ordinary skill in the art would be able to construct the transgenes and vectors of the invention.

The invention further includes a knock-in targeting vector comprising a nucleic acid encoding a selectable marker such as, for example, a nucleic acid encoding the neo$^R$ gene thereby allowing the selection of transgenic a cell where the nucleic acid encoding thrombin resistant FGF-1, or a portion thereof, has inserted along with the neomycin resistance gene by the cell's ability to grow in the presence of G418. However, the present invention should not be construed to be limited to neomycin resistance as a selectable marker. Rather, other selectable markers well-known in the art may be used in targeting vector to allow selection of recombinant cells where the thrombin resistant FGF-1 gene has been inserted along with a nucleic acid encoding the selectable marker of choice. Methods of selecting and incorporating a selectable marker into a vector are well-known in the art and are describe in, for example, Sambrook et al. (1989, Molecular Cloning: A Laboratory Manual, Cold Spring Harbor Laboratory, New York), and in Ausubel et al. (1997, Current Protocols in Molecular Biology, John Wiley & Sons, New York).

As noted herein, the invention includes a transgenic non-human mammal wherein an exogenous nucleic acid encoding thrombin resistant FGF-1 is inserted into a site the genome, i.e., a "knock-in" transgenic mammal. The knock-in transgene inserted may comprise various nucleic acids encoding, for example, a tag polypeptide, a promoter/regulatory region operably linked to the nucleic acid encoding thrombin resistant FGF-1 not normally present in the cell or not typically operably linked to thrombin resistant FGF-1.

The generation of the non-human transgenic mammal of the invention is preferably accomplished using the method which is now described. However, the invention should in no way be construed as being limited solely to the use of this method, in that, other methods can be used to generate the desired transgenic non-human mammal.

In the preferred method of generating a non-human transgenic mammal, ES cells are generated comprising the transgene of the invention and the cells are then used to generate the knock-out animal essentially as described in Nagy and Rossant (1993, In: Gene Targeting, A Practical Approach, pp. 146–179, Joyner ed., IRL Press). ES cells behave as normal embryonic cells if they are returned to the embryonic environment by injection into a host blastocyst or aggregate with blastomere stage embryos. When so returned, the cells have the full potential to develop along all lineages of the embryo. Thus, it is possible, to obtain ES cells, introduce a desired DNA therein, and then return the cell to the embryonic environment for development into mature mammalian cells, wherein the desired DNA may be expressed.

Precise protocols for the generation of transgenic mice are disclosed in Nagy and Rossant (1993, In: Gene Targeting, A Practical Approach, Joyner ed. IRL Press, pp. 146–179). and are therefore not repeated herein. Transfection or transduction of ES cells in order to introduce the desired DNA therein is accomplished using standard protocols, such as those described, for example, in Sambrook et al. (1989, In: Molecular Cloning: A Laboratory Manual, Cold Spring Harbor Laboratory, New York), and in Ausubel et al. (1997, Current Protocols in Molecular Biology, John Wiley & Sons, New York). Preferably, the desired DNA contained within the transgene of the invention is electroporated into ES cells, and the cells are propagated as described in Soriano et al. (1991, Cell 64:693–702).

Introduction of an isolated nucleic acid into the fertilized egg of the mammal is accomplished by any number of standard techniques in transgenic technology (Hogan et al., 1986, Manipulating the Mouse Embryo: A Laboratory Manual, Cold Spring Harbor, N.Y.). Most commonly, the nucleic acid is introduced into the embryo by way of microinjection.

Once the nucleic acid is introduced into the egg, the egg is incubated for a short period of time and is then transferred into a pseudopregnant mammal of the same species from which the egg was obtained as described, for example, in Hogan et al. (1986, Manipulating the Mouse Embryo: A Laboratory Manual, Cold Spring Harbor, N.Y.). Typically, many eggs are injected per experiment, and approximately two-thirds of the eggs survive the procedure. About twenty viable eggs are then transferred into pseudopregnant animals, and usually four to ten of the viable eggs so transferred will develop into live pups.

Any mammalian thrombin resistant FGF-1 gene may be used in the methods described herein to produce a transgenic mammal or a transgenic cell harboring a transgene comprising a deletion of all or part of that mammalian thrombin resistant FGF-1 gene. Preferably, a human thrombin resistant FGF-1 is used.

The transgenic mammal of the invention can be any species of mammal. Thus, the invention should be construed to include generation of transgenic mammals encoding the chimeric nucleic acid, which mammals include mice, hamsters, rats, rabbits, pigs, sheep and cattle. The methods described herein for generation of transgenic mice can be analogously applied using any mammalian species. Preferably, the transgenic mammal of the invention is a rodent and even more preferably, the transgenic mammal of the invention is a mouse. By way of example, Lukkarinen et al. (1997, Stroke 28:639–645), teaches that gene constructs which enable the generation of transgenic mice also enable the generation of other transgenic rodents, including rats. Similarly, nullizygous mutations in a genetic locus of an animal of one species can be replicated in an animal of another species having a genetic locus highly homologous to the first species.

To identify the transgenic mammals of the invention, pups are examined for the presence of the isolated nucleic acid using standard technology such as Southern blot hybridization, PCR, and/or RT-PCR. Expression of the nucleic acid in the cells and in the tissues of the mammal is also assessed using ordinary technology described herein. Further, the presence or absence of thrombin resistant FGF-1 in the circulating blood of the transgenic animal can be determined, for example, as disclosed herein (e.g., cell proliferation assays in the presence or absence of thrombin), or using standard methods for protein detection that are well-known in the art.

Cells obtained from the transgenic mammal of the invention, which are also considered "transgenic cells" as the term is used herein, encompass such as cells as those obtained from the thrombin resistant FGF-1 (+/−) and (−/−) transgenic non-human mammal described elsewhere herein, are useful systems for modeling diseases and symptoms of mammals which are believed to be treatable by administration of FGF-1 which would otherwise be inactivated by thrombin degradation such as, but not limited to myocardial ischemia, peripheral vascular disease, cerebral ischemia, epithelial/epidermal wound injury, and nerve injury.

Particularly suitable are cells derived from a tissue of the non-human transgenic mammal described herein, wherein the transgene comprising the thrombin resistant FGF-1 gene is expressed in various tissues. By way of example, cell types from which such cells are derived include endothelial cells, vascular smooth muscle cells, fibroblasts, epithelial cells, chondrocytes, osteoblasts oligiodendrocytes, and astrocytes, cells of (1) the thrombin resistant FGF-1 (+/+), (+/−) and (−/−) non-human transgenic liveborn mammal, (2) the thrombin resistant FGF-1 (+/+), (−/−) or (+/−) fetal animal, and (3) placental cell lines obtained from the thrombin resistant FGF-1 (+/+), (−/−) and (+/−) fetus and liveborn mammal.

Methods and compositions useful for maintaining mammalian cells in culture are well known in the art, wherein the mammalian cells are obtained from a mammal including, but not limited to, cells obtained from a mouse such as the transgenic mouse described herein, or cells obtained from primate and non-primate mammals.

The recombinant cell of the invention can be used to produce thrombin resistant FGF-1 for use for therapeutic and/or diagnostic purposes. That is, a recombinant cell expressing thrombin resistant FGF-1 can be used to produce large amounts of purified and isolated thrombin resistant FGF-1 that can be administered to treat or alleviate a disease, disorder or condition that would respond to administration of FGF-1 to a cell but wherein the FGF-1 is subject to thrombin degradation.

Alternatively, recombinant cells expressing thrombin resistant FGF-1 can be administered in ex vivo and in vivo therapies where administering the recombinant cells thereby administers the protein to a cell, a tissue, and/or an animal.

The recombinant cell of the invention may be used to study the effects of elevated or decreased thrombin resistant FGF-1 levels on cell homeostasis and cell proliferation since thrombin resistant FGF-1 has been hypothesized to play a role in angiogenesis, nerve regeneration, and tissue repair following injury, and the like V. Antibodies The invention also includes an antibody that specifically binds thrombin resistant FGF-1, or a fragment thereof.

In one embodiment, the antibody is directed to human thrombin resistant FGF-1 comprising the amino acid sequence of SEQ ID NO:4, or an immunogenic portion thereof.

Polyclonal antibodies are generated by immunizing rabbits according to standard immunological techniques well-known in the art (see, e.g., Harlow et al., 1988, In: Antibodies, A Laboratory Manual, Cold Spring Harbor, N.Y.). Such techniques include immunizing an animal with a chimeric protein comprising a portion of another protein such as a maltose binding protein or glutathione (GSH) tag polypeptide portion, and/or a moiety such that the thrombin resistant FGF-1 portion is rendered immunogenic (e.g., thrombin resistant FGF-1 conjugated with keyhole limpet hemocyanin, KLH) and a portion comprising the respective thrombin resistant FGF-1 amino acid residues. The chimeric proteins are produced by cloning the appropriate nucleic acids encoding thrombin resistant FGF-1 (e.g., SEQ ID NO:3) into a plasmid vector suitable for this purpose, such as but not limited to, pMAL-2 or pCMX.

However, the invention should not be construed as being limited solely to these antibodies or to these portions of the protein antigens. Rather, the invention should be construed to include other antibodies, as that term is defined elsewhere herein, to human thrombin resistant FGF-1, or portions thereof. Further, the present invention should be construed to encompass antibodies, inter alia, bind to thrombin resistant FGF-1 and they are able to bind thrombin resistant FGF-1 present on Western blots, in solution in enzyme linked immunoassays, in fluorescence activated cells sorting (FACS) assays, in immunohistochemical staining of tissues thereby localizing thrombin resistant FGF-1 in the tissues, and in immunofluorescence microscopy of a cell transiently transfected with a nucleic acid encoding at least a portion of thrombin resistant FGF-1.

One skilled in the art would appreciate, based upon the disclosure provided herein, that the antibody can specifically bind with any portion of the protein and the full-length protein can be used to generate antibodies specific therefor. However, the present invention is not limited to using the full-length protein as an immunogen. Rather, the present invention includes using an immunogenic portion of the protein to produce an antibody that specifically binds with thrombin resistant FGF-1. That is, the invention includes immunizing an animal using an immunogenic portion, or antigenic determinant, of the thrombin resistant FGF-1 protein.

The antibodies can be produced by immunizing an animal such as, but not limited to, a rabbit or a mouse, with a protein of the invention, or a portion thereof, preferably, the portion comprising the amino acid substitution from arginine to lysine at position number 136 relative to SEQ ID NO:2, e.g., by immunizing an animal using a protein comprising at least a portion of thrombin resistant FGF-1 (e.g., a fragment comprising amino acids from about residue number 120 to 145), or a fusion protein including a tag polypeptide portion comprising, for example, a maltose binding protein tag polypeptide portion, covalently linked with a portion comprising the appropriate thrombin resistant FGF-1 amino acid residues (e.g., amino acids 120–145). One skilled in the art would appreciate, based upon the disclosure provided herein, that smaller fragments of these proteins can also be used to produce antibodies that specifically bind thrombin resistant FGF-1.

One skilled in the art would appreciate, based upon the disclosure provided herein, that various portions of an isolated thrombin resistant FGF-1 polypeptide can be used to generate antibodies to either highly conserved regions of thrombin resistant FGF-1 or to non-conserved regions of the polypeptide including regions containing mutations.

Once armed with the sequence of thrombin resistant FGF-1 and the detailed analysis localizing the various conserved and non-conserved domains of the protein, the skilled artisan would understand, based upon the disclosure provided herein, how to obtain antibodies specific for the various portions of a mammalian thrombin resistant FGF-1 polypeptide using methods well-known in the art or to be developed.

Further, the skilled artisan, based upon the disclosure provided herein, would appreciate that using a non-conserved immunogenic portion can produce antibodies specific for the non-conserved region thereby producing antibodies that do not cross-react with other proteins which can share one or more conserved portions. Thus, one skilled in the art would appreciate, based upon the disclosure provided herein, that the non-conserved regions of thrombin resistant FGF-1 molecule can be used to produce antibodies that are specific only for thrombin resistant FGF-1 and do not cross-react non-specifically with wild type or non-thrombin resistant FGF-1, or with other proteins.

The invention should not be construed as being limited solely to the antibodies disclosed herein or to any particular immunogenic portion of the proteins of the invention. Rather, the invention should be construed to include other antibodies, as that term is defined elsewhere herein, to thrombin resistant FGF-1, or portions thereof. More preferably, the polypeptide that specifically binds with an antibody specific for mammalian thrombin resistant FGF-1 is human thrombin resistant FGF-1 wherein the amino acid at position number 136 relative to SEQ ID NO:2 is lysine. Most preferably, the polypeptide that specifically binds with an antibody that specifically binds with a thrombin resistant FGF-1 is SEQ ID NO: 2.

The invention encompasses polyclonal, monoclonal, synthetic antibodies, and the like. One skilled in the art would understand, based upon the disclosure provided herein, that the crucial feature of the antibody of the invention is that the antibody bind specifically with thrombin resistant FGF-1. That is, the antibody of the invention recognizes thrombin resistant FGF-1, or a fragment thereof (e.g., an immunogenic portion or antigenic determinant thereof), on Western blots, in immunostaining of cells, and immunoprecipitates thrombin resistant FGF-1 using standard methods well-known in the art.

One skilled in the art would appreciate, based upon the disclosure provided herein, that the antibodies can be used to localize the relevant protein in a cell and to study the role(s) of the antigen recognized thereby in cell processes. Moreover, the antibodies can be used to detect and or measure the amount of protein present in a biological sample using well-known methods such as, but not limited to, Western blotting and enzyme-linked immunosorbent assay (ELISA). Moreover, the antibodies can be used to immunoprecipitate and/or immuno-affinity purify their cognate antigen using methods well-known in the art. In addition, the antibody can be used to decrease the level of thrombin resistant FGF-1 in a cell thereby inhibiting the effect(s) of thrombin resistant FGF-1 in a cell. Thus, by administering the antibody to a cell or to the tissues of an animal or to the animal itself, the required thrombin resistant FGF-1 receptor/ligand interactions are therefore inhibited such that the effect of thrombin resistant FGF-1 mediated signaling are also inhibited. One skilled in the art would understand, based upon the disclosure provided herein, that detectable effects upon inhibiting thrombin resistant FGF-1 protein/nucleic acid binding interaction using an anti-thrombin resistant FGF-1 antibody can include, but are not limited to, decreased proliferation of FGF-1 responsive cells, and the like.

The skilled artisan would appreciate, based upon the disclosure provided herein, that that present invention includes use of either a single antibody recognizing a single thrombin resistant FGF-1 epitope but that the invention is not limited to use of a single antibody. Instead, the invention encompasses use of at least one antibody where the antibodies can be directed to the same or different thrombin resistant FGF-1 epitopes.

The generation of polyclonal antibodies is accomplished by inoculating the desired animal with the antigen and isolating antibodies which specifically bind the antigen therefrom using standard antibody production methods such as those described in, for example, Harlow et al. (1988, In: Antibodies, A Laboratory Manual, Cold Spring Harbor, N.Y.).

Monoclonal antibodies directed against full length or peptide fragments of a protein or peptide may be prepared using any well known monoclonal antibody preparation procedures, such as those described, for example, in Harlow et al. (1988, In: Antibodies, A Laboratory Manual, Cold Spring Harbor, N.Y.) and in Tuszynski et al. (1988, Blood, 72:109–115). Quantities of the desired peptide may also be synthesized using chemical synthesis technology. Alternatively, DNA encoding the desired peptide may be cloned and expressed from an appropriate promoter sequence in cells suitable for the generation of large quantities of peptide. Monoclonal antibodies directed against the peptide are generated from mice immunized with the peptide using standard procedures as referenced herein.

Nucleic acid encoding the monoclonal antibody obtained using the procedures described herein may be cloned and sequenced using technology which is available in the art, and is described, for example, in Wright et al. (1992, Critical Rev. Immunol. 12:125–168), and the references cited therein.

Further, the antibody of the invention may be "humanized" using the technology described in, for example, Wright et al., id., and in the references cited therein, and in Gu et al. (1997, Thrombosis and Hematocyst 77:755–759), and other methods of humanizing antibodies well-known in the art or to be developed.

To generate a phage antibody library, a cDNA library is first obtained from mRNA which is isolated from cells, e.g., the hybridoma, which express the desired protein to be expressed on the phage surface, e.g., the desired antibody. cDNA copies of the mRNA are produced using reverse transcriptase. cDNA which specifies immunoglobulin fragments are obtained by PCR and the resulting DNA is cloned into a suitable bacteriophage vector to generate a bacteriophage DNA library comprising DNA specifying immunoglobulin genes. The procedures for making a bacteriophage library comprising heterologous DNA are well known in the art and are described, for example, in Sambrook et al., supra.

Bacteriophage which encode the desired antibody, may be engineered such that the protein is displayed on the surface thereof in such a manner that it is available for binding to its corresponding binding protein, e.g., the antigen against which the antibody is directed. Thus, when bacteriophage which express a specific antibody are incubated in the presence of a cell which expresses the corresponding antigen, the bacteriophage will bind to the cell. Bacteriophage which do not express the antibody will not bind to the cell. Such panning techniques are well known in the art and are described for example, in Wright et al. (supra).

Processes such as those described above, have been developed for the production of human antibodies using M13 bacteriophage display (Burton et al., 1994, Adv. Immunol. 57:191–280). Essentially, a cDNA library is generated from mRNA obtained from a population of antibody-producing cells. The mRNA encodes rearranged immunoglobulin genes and thus, the cDNA encodes the same. Amplified cDNA is cloned into M13 expression vectors creating a library of phage which express human Fab fragments on their surface. Phage which display the antibody of interest are selected by antigen binding and are propagated in bacteria to produce soluble human Fab immunoglobulin. Thus, in contrast to conventional monoclonal antibody synthesis, this procedure immortalizes DNA encoding human immunoglobulin rather than cells which express human immunoglobulin.

The procedures just presented describe the generation of phage which encode the Fab portion of an antibody molecule. However, the invention should not be construed to be limited solely to the generation of phage encoding Fab antibodies. Rather, phage which encode single chain antibodies (scFv/phage antibody libraries) are also included in the invention. Fab molecules comprise the entire Ig light chain, that is, they comprise both the variable and constant region of the light chain, but include only the variable region and first constant region domain (CHI) of the heavy chain. Single chain antibody molecules comprise a single chain of protein comprising the Ig Fv fragment. An Ig Fv fragment includes only the variable regions of the heavy and light chains of the antibody, having no constant region contained therein. Phage libraries comprising scFv DNA may be generated following the procedures described in Marks et al. (1991, J. Mol. Biol. 222:581–597). Panning of phage so generated for the isolation of a desired antibody is conducted in a manner similar to that described for phage libraries comprising Fab DNA.

The invention should also be construed to include synthetic phage display libraries in which the heavy and light chain variable regions may be synthesized such that they include nearly all possible specificities (Barbas, 1995, Nature Medicine 1:837–839; de Kruif et al. 1995, J. Mol. Biol. 248:97–105).

VI. Compositions

The invention includes a composition comprising an isolated nucleic encoding a thrombin resistant FGF-1. Preferably, the composition comprises a pharmaceutically acceptable carrier.

The invention includes a composition comprising an isolated thrombin resistant FGF-1 polypeptide as described herein. Preferably, the composition comprises a pharmaceutically-acceptable carrier.

The invention also includes a composition comprising an antibody that specifically binds thrombin resistant FGF-1. Preferably, the composition comprises a pharmaceutically-acceptable carrier.

The invention further includes a composition comprising an isolated nucleic acid encoding a mammalian thrombin resistant FGF-1. Preferably, the composition comprises a pharmaceutically acceptable carrier. The compositions can be used to administer thrombin resistant FGF-1, and/or a nucleic acid encoding the protein, to a cell, a tissue, or an animal.

The compositions are useful to treat a disease, disorder or condition which would respond to administration of FGF-1, but wherein FGF-1 is degraded by thrombin such that administering thrombin resistant FGF-1 would allow the administration of biologically active FGF-1 to a cell or tissue where the effects of the FGF-1 contacting the cells would provide a benefit to the cell or tissue. That is, where a disease, disorder or condition in an animal would be alleviated or treated by FGF-1 contacting a cell where such contacting would otherwise be inhibited by thrombin degradation of the FGF-1, the composition can be used to administer biologically active FGF-1 to the cell in that the FGF-1 is resistant to thrombin degradation.

One skilled in the art would understand, based on the disclosure provided herein, that thrombin resistant FGF-1 can be administered to a cell or tissue by administering the protein itself or by administering a nucleic acid encoding the protein. Either way, thrombin resistant FGF-1 is administered to the cell and/or tissue.

For administration to the mammal, a polypeptide, or a nucleic acid encoding it, can be suspended in any pharmaceutically acceptable carrier, for example, HEPES buffered saline at a pH of about 7.8.

The skilled artisan would further appreciate, based upon the disclosure provided herein, that the invention encompasses compositions comprising at least one of a nucleic acid encoding thrombin resistant FGF-1, an isolated thrombin resistant FGF-1 polypeptide, or a portion thereof.

One skilled in the art would understand, based upon the instant disclosure, that compositions comprising mixtures of the above-discussed compounds, i.e., nucleic acids encoding thrombin resistant FGF-1, and thrombin resistant FGF-1 polypeptides, and the like, are encompassed in the invention.

Additionally, compositions comprising at least one of the afore-mentioned compounds where the compositions further comprise additional compounds, such as, but not limited to, heparin or heparin-like molecules (e.g., heparin sulfate, and the like), drugs, ionic agents (e.g., calcium chloride), and the like, are also contemplated in the present invention. One skilled in the art would appreciate, based upon the disclosure provided herein, that such compositions are useful for treatment of diseases, disorders, or conditions that can be treated or alleviated by administration of thrombin resistant FGF-1.

Other pharmaceutically acceptable carriers which are useful include, but are not limited to, glycerol, water, saline, ethanol and other pharmaceutically acceptable salt solutions such as phosphates and salts of organic acids. Examples of these and other pharmaceutically acceptable carriers are described in Remington's Pharmaceutical Sciences (1991, Mack Publication Co., New Jersey).

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides.

Pharmaceutical compositions that are useful in the methods of the invention may be administered, prepared, packaged, and/or sold in formulations suitable for oral, rectal, vaginal, parenteral, topical, pulmonary, intranasal, buccal, ophthalmic, or another route of administration. Other contemplated formulations include projected nanoparticles, liposomal preparations, resealed erythrocytes containing the active ingredient, and immunologically-based formulations.

The compositions of the invention may be administered via numerous routes, including, but not limited to, oral, rectal, vaginal, parenteral, topical, pulmonary, intranasal, buccal, intracoronary, or pericardial administration routes. The route(s) of administration will be readily apparent to the skilled artisan and will depend upon any number of factors including the type and severity of the disease being treated, the type and age of the veterinary or human patient being treated, and the like.

Pharmaceutical compositions that are useful in the methods of the invention may be administered systemically in oral solid formulations, ophthalmic, suppository, aerosol, topical or other similar formulations. In addition to the compound such as heparan sulfate, or a biological equivalent thereof, such pharmaceutical compositions may contain pharmaceutically-acceptable carriers and other ingredients known to enhance and facilitate drug administration. Other possible formulations, such as fibrin sealant, synthetic polymers, nanoparticles, liposomes, resealed erythrocytes, and immunologically based systems may also be used to administer thrombin resistant FGF-1 and/or a nucleic acid encoding the same according to the methods of the invention.

Compounds which are identified using any of the methods described herein may be formulated and administered to a mammal for treatment of myocardial ischemia are now described.

The invention encompasses the preparation and use of pharmaceutical compositions comprising a compound useful for treatment of myocardial ischemia as an active ingredient. Such a pharmaceutical composition may consist of the active ingredient alone, in a form suitable for administration to a subject, or the pharmaceutical composition may comprise the active ingredient and one or more pharmaceutically acceptable carriers, one or more additional ingredients, or some combination of these. The active ingredient may be present in the pharmaceutical composition in the form of a physiologically acceptable ester or salt, such as in combination with a physiologically acceptable cation or anion, as is well known in the art.

As used herein, the term "pharmaceutically acceptable carrier" means a chemical composition with which the active ingredient may be combined and which, following the combination, can be used to administer the active ingredient to a subject.

As used herein, the term "physiologically acceptable" ester or salt means an ester or salt form of the active ingredient which is compatible with any other ingredients of the pharmaceutical composition, which is not deleterious to the subject to which the composition is to be administered.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

Although the descriptions of pharmaceutical compositions provided herein are principally directed to pharmaceutical compositions which are suitable for ethical administration to humans, it will be understood by the skilled artisan that such $_1\mu g$ compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, mammals including commercially relevant mammals such as cattle, pigs, horses, sheep, cats, and dogs.

Pharmaceutical compositions that are useful in the methods of the invention may be prepared, packaged, or sold in formulations suitable for oral, rectal, vaginal, parenteral, topical, pulmonary, intranasal, buccal, intrathecal or another route of administration. Other contemplated formulations include projected nanoparticles, liposomal preparations, resealed erythrocytes containing the active ingredient, and immunologically-based formulations.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

In addition to the active ingredient, a pharmaceutical composition of the invention may further comprise one or more additional pharmaceutically active agents. Particularly contemplated additional agents include anti-emetics and scavengers such as cyanide and cyanate scavengers.

Controlled- or sustained-release formulations of a pharmaceutical composition of the invention may be made using conventional technology.

A formulation of a pharmaceutical composition of the invention suitable for oral administration may be prepared, packaged, or sold in the form of a discrete solid dose unit including, but not limited to, a tablet, a hard or soft capsule, a cachet, a troche, or a lozenge, each containing a predetermined amount of the active ingredient. Other formulations suitable for oral administration include, but are not limited to, a powdered or granular formulation, an aqueous or oily suspension, an aqueous or oily solution, or an emulsion.

As used herein, an "oily" liquid is one which comprises a carbon-containing liquid molecule and which exhibits a less polar character than water.

A tablet comprising the active ingredient may, for example, be made by compressing or molding the active ingredient, optionally with one or more additional ingredients. Compressed tablets may be prepared by compressing, in a suitable device, the active ingredient in a free-flowing form such as a powder or granular preparation, optionally mixed with one or more of a binder, a lubricant, an excipient, a surface active agent, and a dispersing agent. Molded tablets may be made by molding, in a suitable device, a mixture of the active ingredient, a pharmaceutically acceptable carrier, and at least sufficient liquid to moisten the mixture. Pharmaceutically acceptable excipients used in the manufacture of tablets include, but are not limited to, inert diluents, granulating and disintegrating agents, binding agents, and lubricating agents. Known dispersing agents include, but are not limited to, potato starch and sodium starch glycollate. Known surface active agents include, but are not limited to, sodium lauryl sulphate. Known diluents include, but are not limited to, calcium carbonate, sodium carbonate, lactose, microcrystalline cellulose, calcium phosphate, calcium hydrogen phosphate, and sodium phosphate. Known granulating and disintegrating agents include, but are not limited to, corn starch and alginic acid. Known binding agents include, but are not limited to, gelatin, acacia, pre-gelatinized maize starch, polyvinylpyrrolidone, and hydroxypropyl methylcellulose. Known lubricating agents include, but are not limited to, magnesium stearate, stearic acid, silica, and talc.

Tablets may be non-coated or they may be coated using known methods to achieve delayed disintegration in the gastrointestinal tract of a subject, thereby providing sustained release and absorption of the active ingredient. By way of example, a material such as glyceryl monostearate or glyceryl distearate may be used to coat tablets. Further by way of example, tablets may be coated using methods described in U.S. Pat. Nos. 4,256,108; 4,160,452; and 4,265,874 to form osmotically-controlled release tablets. Tablets may further comprise a sweetening agent, a flavoring agent, a coloring agent, a preservative, or some combination of these in order to provide pharmaceutically elegant and palatable preparation.

Hard capsules comprising the active ingredient may be made using a physiologically degradable composition, such as gelatin. Such hard capsules comprise the active ingredient, and may further comprise additional ingredients including, for example, an inert solid diluent such as calcium carbonate, calcium phosphate, or kaolin.

Soft gelatin capsules comprising the active ingredient may be made using a physiologically degradable composition, such as gelatin. Such soft capsules comprise the active ingredient, which may be mixed with water or an oil medium such as peanut oil, liquid paraffin, or olive oil.

Liquid formulations of a pharmaceutical composition of the invention which are suitable for oral administration may be prepared, packaged, and sold either in liquid form or in the form of a dry product intended for reconstitution with water or another suitable vehicle prior to use.

Liquid suspensions may be prepared using conventional methods to achieve suspension of the active ingredient in an aqueous or oily vehicle. Aqueous vehicles include, for example, water and isotonic saline. Oily vehicles include, for example, almond oil, oily esters, ethyl alcohol, vegetable oils such as arachis, olive, sesame, or coconut oil, fractionated vegetable oils, and mineral oils such as liquid paraffin. Liquid suspensions may further comprise one or more additional ingredients including, but not limited to, suspending agents, dispersing or wetting agents, emulsifying agents, demulcents, preservatives, buffers, salts, flavorings, coloring agents, and sweetening agents. Oily suspensions may further comprise a thickening agent. Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, hydroxypropylmethylcellulose. Known dispersing or wetting agents include, but are not limited to, naturally-occurring phosphatides such as lecithin, condensation products of an alkylene oxide with a fatty acid, with a long chain aliphatic alcohol, with a partial ester derived from a fatty acid and a hexitol, or with a stearate, heptadecaethyleneoxycetanol, polyoxyethylene sorbitol monooleate, and polyoxyethylene sorbitan monooleate, respectively). Known emulsifying agents include, but are not limited to, lecithin and acacia. Known preservatives include, but are not limited to, methyl, ethyl, or n-propyl-para-hydroxybenzoates, ascorbic acid, and sorbic acid. Known sweetening agents include, for example, glycerol, propylene glycol, sorbitol, sucrose, and saccharin. Known thickening agents for oily suspensions include, for example, beeswax, hard paraffin, and cetyl alcohol.

Liquid solutions of the active ingredient in aqueous or oily solvents may be prepared in substantially the same manner as liquid suspensions, the primary difference being that the active ingredient is dissolved, rather than suspended in the solvent. Liquid solutions of the pharmaceutical composition of the invention may comprise each of the components described with regard to liquid suspensions, it being understood that suspending agents will not necessarily aid dissolution of the active ingredient in the solvent. Aqueous solvents include, for example, water and isotonic saline. Oily solvents include, for example, almond oil, oily esters, ethyl alcohol, vegetable oils such as arachis, olive, sesame, or coconut oil, fractionated vegetable oils, and mineral oils such as liquid paraffin.

Powdered and granular formulations of a pharmaceutical preparation of the invention may be prepared using known methods. Such formulations may be administered directly to a subject, used, for example, to form tablets, to fill capsules, or to prepare an aqueous or oily suspension or solution by addition of an aqueous or oily vehicle thereto. Each of these formulations may further comprise one or more of dispersing or wetting agent, a suspending agent, and a preservative. Additional excipients, such as fillers and sweetening, flavoring, or coloring agents, may also be included in these formulations.

A pharmaceutical composition of the invention may also be prepared, packaged, or sold in the form of oil-in-water emulsion or a water-in-oil emulsion. The oily phase may be a vegetable oil such as olive or arachis oil, a mineral oil such as liquid paraffin, or a combination of these. Such compositions may further comprise one or more emulsifying agents such as naturally occurring gums such as gum acacia or gum tragacanth, naturally-occurring phosphatides such as soybean or lecithin phosphatide, esters or partial esters derived from combinations of fatty acids and hexitol anhydrides such as sorbitan monooleate, and condensation products of such partial esters with ethylene oxide such as polyoxyethylene sorbitan monooleate. These emulsions may also contain additional ingredients including, for example, sweetening or flavoring agents.

A pharmaceutical composition of the invention may be prepared, packaged, or sold in a formulation suitable for rectal administration. Such a composition may be in the form of, for example, a suppository, a retention enema preparation, and a solution for rectal or colonic irrigation.

Suppository formulations may be made by combining the active ingredient with a non-irritating pharmaceutically acceptable excipient which is solid at ordinary room temperature (i.e., about 20° C.) and which is liquid at the rectal temperature of the subject (i.e., about 37° C. in a healthy human). Suitable pharmaceutically acceptable excipients include, but are not limited to, cocoa butter, polyethylene glycols, and various glycerides. Suppository formulations may further comprise various additional ingredients including, but not limited to, antioxidants and preservatives.

Retention enema preparations or solutions for rectal or colonic irrigation may be made by combining the active ingredient with a pharmaceutically acceptable liquid carrier. As is well known in the art, enema preparations may be administered using, and may be packaged within, a delivery device adapted to the rectal anatomy of the subject. Enema preparations may further comprise various additional ingredients including, but not limited to, antioxidants and preservatives.

A pharmaceutical composition of the invention may be prepared, packaged, or sold in a formulation suitable for vaginal administration. Such a composition may be in the form of, for example, a suppository, an impregnated or coated vaginally-insertable material such as a tampon, a douche preparation, or gel or cream or a solution for vaginal irrigation.

Methods for impregnating or coating a material with a chemical composition are known in the art, and include, but are not limited to methods of depositing or binding a chemical composition onto a surface, methods of incorporating a chemical composition into the structure of a material during the synthesis of the material (i.e., such as with a physiologically degradable material), and methods of absorbing an aqueous or oily solution or suspension into an absorbent material, with or without subsequent drying.

Douche preparations or solutions for vaginal irrigation may be made by combining the active ingredient with a pharmaceutically acceptable liquid carrier. As is well known in the art, douche preparations may be administered using, and may be packaged within, a delivery device adapted to the vaginal anatomy of the subject. Douche preparations may further comprise various additional ingredients including, but not limited to, antioxidants, antibiotics, antifungal agents, and preservatives.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, intrastemal injection, intracoronary, pericardially, intracardial, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e., powder or granular) form for reconstitution with a suitable vehicle (e.g., sterile pyrogen-free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient in microcrystalline form, in a liposomal preparation, or as a component of a biodegradable polymer systems. Compositions for sustained release or implantation may comprise pharmaceutically acceptable polymeric or hydrophobic materials such as an emulsion, an ion exchange resin, a sparingly soluble polymer, or a sparingly soluble salt.

Formulations suitable for topical administration include, but are not limited to, liquid or semi-liquid preparations such as liniments, lotions, oil-in-water or water-in-oil emulsions such as creams, ointments or pastes, and solutions or suspensions. Topically-administrable formulations may, for example, comprise from about 1% to about 10% (w/w) active ingredient, although the concentration of the active ingredient may be as high as the solubility limit of the active ingredient in the solvent. Formulations for topical administration may further comprise one or more of the additional ingredients described herein.

A pharmaceutical composition of the invention may be prepared, packaged, or sold in a formulation suitable for pulmonary administration via the buccal cavity. Such a formulation may comprise dry particles which comprise the active ingredient and which have a diameter in the range from about 0.5 to about 7 nanometers, and preferably from about 1 to about 6 nanometers. Such compositions are conveniently in the form of dry powders for administration using a device comprising a dry powder reservoir to which a stream of propellant may be directed to disperse the powder or using a self-propelling solvent/powder-dispensing container such as a device comprising the active ingredient dissolved or suspended in a low-boiling propellant in a sealed container. Preferably, such powders comprise particles wherein at least 98% of the particles by weight have a diameter greater than 0.5 nanometers and at least 95% of the particles by number have a diameter less than 7 nanometers. More preferably, at least 95% of the particles by weight have a diameter greater than 1 nanometer and at least 90% of the particles by number have a diameter less than 6 nanometers. Dry powder compositions preferably include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic or solid anionic surfactant or a solid diluent (preferably having a particle size of the same order as particles comprising the active ingredient).

Pharmaceutical compositions of the invention formulated for pulmonary delivery may also provide the active ingredient in the form of droplets of a solution or suspension. Such formulations may be prepared, packaged, or sold as aqueous or dilute alcoholic solutions or suspensions, optionally sterile, comprising the active ingredient, and may conveniently be administered using any nebulization or atomization device. Such formulations may further comprise one or more additional ingredients including, but not limited to, a flavoring agent such as saccharin sodium, a volatile oil, a buffering agent, a surface active agent, or a preservative such as methylhydroxybenzoate. The droplets provided by this route of administration preferably have an average diameter in the range from about 0.1 to about 200 nanometers.

The formulations described herein as being useful for pulmonary delivery are also useful for intranasal delivery of a pharmaceutical composition of the invention.

Another formulation suitable for intranasal administration is a coarse powder comprising the active ingredient and having an average particle from about 0.2 to 500 micrometers. Such a formulation is administered in the manner in which snuff is taken, i.e., by rapid inhalation through the nasal passage from a container of the powder held close to the nares.

Formulations suitable for nasal administration may, for example, comprise from about as little as 0.1% (w/w) and as much as 100% (w/w) of the active ingredient, and may further comprise one or more of the additional ingredients described herein.

A pharmaceutical composition of the invention may be prepared, packaged, or sold in a formulation suitable for buccal administration. Such formulations may, for example, be in the form of tablets or lozenges made using conventional methods, and may, for example, 0.1 to 20% (w/w) active ingredient, the balance comprising an orally dissolvable or degradable composition and, optionally, one or more of the additional ingredients described herein. Alternately, formulations suitable for buccal administration may comprise a powder or an aerosolized or atomized solution or suspension comprising the active ingredient. Such powdered, aerosolized, or aerosolized formulations, when dispersed, preferably have an average particle or droplet size in the range from about 0.1 to about 200 nanometers, and may further comprise one or more of the additional ingredients described herein.

A pharmaceutical composition of the invention may be prepared, packaged, or sold in a formulation suitable for ophthalmic administration. Such formulations may, for example, be in the form of eye drops including, for example, a 0.1–1.0% (w/w) solution or suspension of the active ingredient in an aqueous or oily liquid carrier. Such drops may further comprise buffering agents, salts, or one or more other of the additional ingredients described herein. Other ophthalmalmically-administrable formulations which are useful include those which comprise the active ingredient in microcrystalline form or in a liposomal preparation.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the invention are known in the art and described, for example in Genaro, ed. (1985, Remington's Pharmaceutical Sciences, Mack Publishing Co., Easton, Pa.), which is incorporated herein by reference.

Typically, dosages of the compound of the invention which may be administered to an animal, preferably a human, will vary depending upon any number of factors, including but not limited to, the type of animal and type of disease state being treated, the age of the animal and the route of administration. The dosages can range from anywhere from as low or lower than 1 pg/kg of body weight to about 100 µg/kg of body weight.

The compound can be administered to an animal as frequently as several times daily, or it may be administered less frequently, such as once a day, once a week, once every two weeks, once a month, or even less frequently, such as once every several months or even once a year or less. The frequency of the dose will be readily apparent to the skilled artisan and will depend upon any number of factors, such as, but not limited to, the type and severity of the disease being treated, the type and age of the animal, etc.

VII. Methods

The present invention includes various methods for the identification and production of mutant FGF-1 resistant to degradation. Further, the invention relates to methods of using such degradation resistant FGF-1 molecules to administer FGF-1 to a site of interest where it would otherwise be degraded.

A. Method of identifying a degradation resistant FGF-1

The invention encompasses a method of identifying degradation resistant FGF-1. The skilled artisan, based upon the disclosure provided herein, would appreciate that there numerous methods for producing mutant molecules of a known protein where the amino acid sequence of the protein is well-known and where the nucleic acid encoding the polypeptide is also known. Thus, the routineer would understand that methods for introducing mutations in the nucleic and/or amino acid sequence of protein, such as those exemplified herein, as well as those well-known in the art or to be developed in the future, can be used to produce mutant FGF-1 molecules that can be assessed for degradation resistance.

Based upon the disclosure provided herein, one skilled in the art would appreciate that mutations can be introduced in the nucleic (SEQ ID NO: 1) and amino acid (SEQ ID NO:2) sequences of wild type FGF-1, and the mutants so produced can be assayed for degradation resistance. That is, the artisan would appreciate, once armed with the teachings provided herein, that certain domains of the FGF-1 protein provide targets for mutagenesis specific for the production of mutant molecules that are potential candidate degradation resistant molecules while preserving the biological activity of the wild type growth factor.

The skilled artisan would further understand, based upon the disclosure provided herein, that the invention encompasses the truncated forms of FGF-1 comprising R136K mutation and further comprising a deletion of from about 14 or 15 amino acid N-terminal residues.

The skilled artisan would further appreciate that the particular methods used to produce the mutant FGF-1 to be assayed for degradation resistance, i.e., the "test FGF-1," are not limited to those exemplified herein. Rather, the invention includes any method for mutagenizing a nucleic and/or amino acid known in the art or to be developed in the future. Such methods include, but are not limited to, those disclosed herein and those to be developed in the future. One skilled in the art would understand, based upon the disclosure provided herein, that a nucleic acid encoding FGF-1 can be mutated to produce a mutant polypeptide. Alternatively, a mutant FGF-1 polypeptide can be synthesized where at least one amino acid is mutated relative to the parent amino acid sequence.

The test FGF-1 is treated under conditions known to degrade wild type FGF-1, or conditions that are known to detectably degrade the parent FGF-1 used as the template for introducing a mutation. Conditions for degrading FGF-1 are well-known in the art, and these include, but are not limited to, exposure to of the test FGF-1 to thrombin, heat, plasmin, extremes in pH, and the like.

Following treatment of the test FGF-1 under conditions known to degrade FGF-1, the biological activity of the test FGF-1 is assessed, and is then compared to the biological activity of wild type FGF-1 which has been treated under identical conditions. Further, the biological activity of test FGF-1 before and after treatment can be compared.

The skilled artisan would appreciate, based upon the disclosure provided herein, that there is a wide plethora of methods for assessing the biological activity of FGF-1. Several such assays are exemplified herein, e.g., assessing the effect of the FGF-1 on cell proliferation which is, in turn, assayed by counting the cells and/or by measuring incorporation of tritiated thymidine into nascent DNA chains. Further, the biological activity of a test FGF-1 following treatment known to degrade FGF-1 can be assessed by examining the protein for any biophysical and/or biochemical changes following treatment. Such assays include, but are not limited to, assessing the molecular mass of the protein using, e.g., gel electrophoresis, analysis, chromatographic methods, and the like. Thus, one skilled in the art would understand, based upon the disclosure provided herein, that the crucial factor is that the test FGF-1 be compared to the wild type, or unmutated, FGF-1 in any assay that assesses the integrity of the molecule, whether the assay detects the biological effect(s) of a test molecule on a cell, or whether the assay detects a physical change in the molecule following a treatment that is known to degrade FGF-1.

B. Methods of using degradation resistant FGF-1

The invention encompasses methods of using a degradation resistant FGF-1 to mediate an FGF-1 associated response in a cell. One skilled in the art would appreciate, based upon the disclosure provided herein, that administration of a degradation resistant FGF-1 provides a critical improvement over prior art methods in that the degradation resistant FGF-1 can be administered and is substantially resistant to being inactivated which would otherwise decrease its activity. In contrast to the non-resistant molecule, a degradation resistant FGF-1 can be administered essentially as is the non-resistant molecule, but, unlike the otherwise identical non-resistant molecule, the degradation resistant FGF-1 is not substantially degraded.

Thus, compared with the non-resistant FGF-1 molecule, a degradation resistant FGF-1 can reach the target cell comprising an FGF-1 receptor on its surface, can mediate a typical FGF-1 response in that cell, and can remain in circulation and/or present at the site of interest, for a period longer than the non-resistant FGF-1, which is degraded while the resistant molecule is not.

The skilled artisan would appreciate, based upon the disclosure provided herein, that a degradation resistant FGF-1, including but not limited to a thrombin degradation resistant FGF-1, can be administered to treat or alleviate any disease or disorder where administration of FGF-1 to a cell would effect a response that would treat or alleviate the disease. Such diseases and disorders are well-known in the art, and include, but are not limited to, myocardial ischemia, peripheral vascular disease, cerebral ischemia, epithelial injury, epidermal wound injury, nerve injury, bone damage, and the like.

The mutant FGF-1 protein in the absence of thrombin has similar activity to wild-type FGF-1. However, in the presence of thrombin displays a much better activity than wild-type. Without wishing to be bound by any particular theory, this is due to the wild-type FGF-1 being degraded by thrombin. Hence the mutant FGF-1 can be used at lower concentration but can exhibit high biological activity in areas where thrombin is present such as sites of injury or ischemia. Mutant thrombin degradation resistant FGF-1 can be used as an angiogenic factor and potential nerve regenerator, as well as to promote wound healing and bone fracture repair.

One skilled in the art would appreciate, based upon the disclosure provided herein, that FGF-1 resistant to various degradations in vivo are encompassed by the present invention. That is, while a FGF-1 resistant to thrombin degradation is exemplified herein, the present invention is not limited to thrombin degradation; instead, the invention includes FGF-1 resistant to, among other things.

Such a degradation resistant FGF-1 molecule can be use to effect an FGF-1 response that is otherwise inhibited by degradation of FGF-1. Thus, the skilled artisan would understand, based upon the disclosure provided herein, that the FGF-1 resistant to thrombin degradation can be used to effect an FGF-1 response that can treat or alleviate a disease or disorder, including, but not limited to, myocardial ischemia, peripheral vascular disease, cerebral ischemia, epithelial injury, epidermal wound injury, nerve injury, and bone damage.

The invention includes a method of enhancing the effectiveness of an FGF-1 response in a mammal where the activity of FGF-1 is decreased or inhibited by thrombin degradation. This is because, as discussed previously elsewhere herein, where the activity of wild-type FGF-1 degraded by thrombin, administration of a thrombin degradation resistant FGF-1 overcomes the inhibition and the resistant molecule effects an FGF-1 response in a cell comprising an FGF-1 receptor on its surface.

The method comprises administering an effective amount of a thrombin degradation resistant FGF-1, or a fragment or derivative thereof, to a mammal. The skilled artisan would appreciate, based upon the disclosure provided herein, that the FGF-1 response is enhanced in that the FGF-1 is not degraded and a higher level of biologically active FGF-1 reaches the cell, and/or, a higher level of biologically active FGF-1 is maintained since the FGF-1 is resistant to degradation and remains active for a longer period of time than the non-resistant FGF-1.

The skilled artisan can readily determine what amount is effective by assessing the level of an FGF-1 response mediated by administration of a degradation resistant molecule using a wide variety of assays, several of which are disclosed herein and others which are well-known in the art or will be developed in the future. Thus, by assessing the level of FGF-1 response mediated by administration of a thrombin degradation resistant FGF-1 and/or by assessing the effects of administration of the resistant FGF-1 on the mammal, e.g., by assessing the effect of administration on a symptom of a disease or condition that responds to administration of FGF-1 to a cell or tissue, one skilled in the relevant art can determine an effective amount of thrombin resistant FGF-1 for a mammal at issue.

The invention includes a method for stimulating an FGF-1 response in a mammal, where the response is otherwise inhibited by degradation of FGF-1. The method comprises administering an effective dose of a degradation resistant FGF-1, or a fragment or derivative thereof, to the mammal. This is because, as more fully set forth previously elsewhere herein, the degradation resistant FGF-1, unlike the non-resistant molecule, can better reach a cell comprising an FGF-1 receptor on its surface since the resistant FGF-1 is not degraded and its half-life in the mammal is increased. Thus, a resistant FGF-1 can be present for a longer period of time and a higher amount of the resistant FGF-1 can reach the cell of interest since it is either not degraded, or is degraded to a lesser extent, than the non-resistant FGF-1.

As disclosed herein, the degradation resistant FGF-1 of the invention can be delivered to a cell or tissue site with decreased, or little, degradation of the protein and/or its activity that would otherwise occur due to thrombin degradation. Thus, the present invention allows the delivery of FGF-1, preferably, biologically active FGF-1, to a site or cell of interest where it would otherwise be degraded due to thrombin proteolysis. Therefore, the routineer would understand, based upon the instant disclosure, that a thrombin-resistant mutant is useful to alleviate and/or treat any disease or disorder that can be ameliorated by administration of FGF-1, especially where thrombin degradation of FGF-1 can inhibit the activity of the FGF-1 which could otherwise effect a beneficial effect at the cell or tissue contacted by FGF-1.

One skilled in the art would appreciate, based upon the disclosure provided herein, that the invention is not limited solely to these diseases or disorders; rather, a wide variety of fibroblast growth factor-1 related diseases or disorders, wherein contacting a cell or tissue with FGF-1 can alleviate or treat the disease or disorder, are encompassed in the invention. The diseases or disorders include those well-known in the art and such diseases or disorders that are at present unknown and to be discovered.

The invention relates to the administration of a composition comprising an isolated nucleic acid encoding mutant FGF-1, and/or a polypeptide encoded thereby, to practice the methods of the invention. The composition comprising the isolated nucleic acid or polypeptide, or a mutant, derivative, or fragment of the isolated nucleic acid or polypeptide, can further comprise a pharmaceutically-acceptable carrier as more fully set forth previously elsewhere herein.

It will be recognized by one of skill in the art that the various embodiments of the invention as described above relating to methods of treating fibroblast growth factor responsive or treatable diseases and disorders encompasses the use of degradation resistant FGFs, or mutants, fragments, or derivatives thereof, as well as other molecules not described herein. Thus, it should not be construed that embodiments described herein do not apply to other forms of FGF-1s or other FGF-1 treatable diseases and disorders.

VIII. Kits

The invention includes various kits which comprise a compound, such as a nucleic acid encoding mutant FGF-1, an isolated mutant FGF-1 polypeptide, and the like, and an applicator, and instructional materials which describe use of the compound to perform the methods of the invention. Although exemplary kits are described below, the contents of other useful kits will be apparent to the skilled artisan in light of the present disclosure. Each of these kits is included within the invention.

In one aspect, the invention includes a kit for alleviating a disease or disorder that responds to administration of FGF-1. The kit is used pursuant to the methods disclosed in the invention. Briefly, the kit may be used to contact a cell with an isolated mutant FGF-1 polypeptide, or with a nucleic acid encoding a mutant FGF-1 which is expressed when contacted with the cell, wherein the mutant FGF-1 is resistant to thrombin degradation and can effect a beneficial effect. Moreover, the kit comprises an applicator and an instructional material for the use of the kit. These instructions simply embody the examples provided herein.

The kit includes a phammaceutically-acceptable carrier. The composition is provided in an appropriate amount as set forth elsewhere herein. Further, the route of administration and the frequency of administration are as previously set forth elsewhere herein.

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

EXAMPLES

Using site directed mutagenesis, a mutant thrombin-resistant FGF-1 was produced wherein an amino acid in a recombinant human wild-type/native FGF-1 protein sequence (SEQ ID NO: 1) was changed, specifically the arginine at position 136 was changed to lysine (FIG. 1). The resulting mutant protein, FGF-1$_{R136K}$ (SEQ ID NO:2), retained the biological activity of wild-type FGF-1 but was much less susceptible to thrombin cleavage. The thrombin-resistant FGF-1$_{R136K}$ mutant is an ideal candidate for therapeutic use of FGF-1, which is otherwise degraded by thrombin.

The Materials and Methods used in the present study are now described.

FGF-1$_{R136K}$ Mutant FGF-1 Construction and Purification

To produce the thrombin-resistant FGF-1 mutant, the full length (beta) form of wild type human FGF-1 was mutated. The full length FGF-1 DNA sequence encodes for a 154 amino acid form of the FGF-1 protein (FIG. 1). The recombinant FGF-1 gene was obtained from Fisheroligo (Fisher Scientific, Pittsburgh, Pa.) and was inserted into the double-stranded plasmid vector, pET3c (Novagen, Madison, Wis.) and this is referred to as the target plasmid DNA. The target plasmid DNA was double-stranded and methylated.

Generation of the FGF-1$_{R136K}$ Mutant

The MORPH™ Site-Specific Plasmid DNA Mutagenesis Kit (Eppendorf 5 Prime, Inc., Boulder, Colo.) was used per manufacturer's instructions to generate the FGF-1$_{R136K}$ mutant. The requirements for this system are that the double-stranded DNA is methylated and that there is at least one Dpn I restriction site present.

The mutagenic oligonucleotide primer (31 base pairs, corresponding to nucleic acid positions 430–460; SEQ ID NO:7) was obtained from Fisheroligo and it consisted of one codon change from wild type so that the amino acid at position 136 would be changed from arginine to lysine. That is, the wild type sequence:

```
CAAACGCGGTCCTCGGACTCACTATGGCCAG    (SEQ ID NO:5)
  K   R   G   P   R   T   H   Y   G   Q    (SEQ ID NO:6)
``` was changed to the oligonucleotide:

```
CAAACGCGGTCCTAAAACTCACTATGGCCAG    (SEQ ID NO:7)
  K   R   G   P   K   T   H   Y   G   Q    (SEQ ID NO:8)
```

The mutagenic oligonucleotide primer (SEQ ID NO:7) was phosphorylated at the 5' end by incubating the mutated oligonucleotide in the presence of T4 polynucleotide kinase for 1 hour at 37° C. The reaction was terminated by heating at 65° C. for 10 minutes.

The target plasmid DNA and phosphorylated mutagenic oligonucleotide were mixed together and denatured by incubation at 100° C. for 5 minutes. The denatured mixture was placed in an ice-water bath for 5 minutes and then incubated at room temperature for 30 minutes. This allowed the mutagenic oligonucleotide to anneal to the correct location on the target plasmid DNA. After the 30 minute incubation, the mixture was placed on ice.

To the annealed reaction mixture, the following was added: T4 DNA polymerase, T4 DNA ligase, and free nucleotide bases. This mixture was mixed and allowed to incubate at 37° C. for 2 hours. This allowed the annealed mutagenic oligonucleotide to be extended and ligated. The reaction was stopped by heating to 85° C. for 15 minutes and then placed on ice.

The resulting mixture contained both non-mutagenized target plasmid DNA, where both strands were methylated, and mutagenized plasmid DNA, which had one original methylated template and one non-methylated replacement strand. The non-mutagenized methylated target plasmid DNA was digested with the restriction enzyme Dpn I, which was added for 30 minutes at 37° C. Placing the mixture on ice for 5 minutes stopped the digestion.

The mixture of mutagenized plasmid DNA and digested DNA was incubated with competent *Escherichia coli* MORPH mut S (*E. coli* mut S) cells on ice for 20 minutes. Bacterial transformation was induced by heat shocking the cells at 42° C. for 2 minutes and then allowing them to cool to room temperature. The transformed cells were spread onto LB agar plates containing carbenicillin and chloramphenicol and incubated at 37° C. for 16 hours. Only transformed cells containing the mutagenized plasmid DNA will grow due to the ampicillin-resistant (Amp$^R$) gene in the pET3c plasmid.

The resulting mutagenized plasmid DNA was isolated from the bacterial colonies and transformed into the BL2]-pLysS strain of E. coli cells, which is a more stable cell line. Stock cultures of transformed BL21-pLysS cells were expanded and then stored in glycerol at −70° C. In addition the mutagenized plasmid DNA was sequenced to confirm that it contained the FGF-$1_{R136K}$ mutation.

For FGF-$1_{R136K}$ protein production and purification the following procedure was performed. A streak of transformed BL21-pLysS cells was added to LB broth containing 100 µg/ml carbenicillin and 34 µg/ml chloramphenicol and incubated overnight with vigorous shaking at 37° C. The overnight culture was diluted with antibiotic-free LB broth and added to an appropriate sized flask. The culture was shaken (250 rpm) at 37° C. until the optical density of the culture, measured at a wavelength of 600 nm, reached 0.4–1.0. The culture was induced to produce the mutant FGF-1 by incubating the cells with 0.4 mM IPTG for 3 hours at 37° C., with shaking. The cells were collected by centrifugation at 8,000 rpm for 10 minutes at 4° C. The supernatant was discarded and the cell pellet was frozen at −70° C.

The frozen pellet was resuspended in heparin-sepharose buffer (50 mM Tris, 10 mM EDTA, pH 7.4). The pellet was whisked into a suspension and then sonicated to break up the cells and to shear the DNA. The resulting cell lysate was centrifuged at 9,000 rpm for 10 minutes at 4° C. The supernatant was added to a heparin-sepharose column and was eluted with step-wise salt concentration of heparin-sepharose buffer containing (0, 0.2, 0.5, 0.8 and 1.5 M NaCl). The FGF-$1_{R136K}$ FGF-1 protein eluted with 1.5 M NaCl as confirmed by SDS-polyacrylamide gel electrophoresis. The fractions containing FGF-$1_{R136K}$ protein were pooled and further purified by reverse phase HPLC using a Jupiter 10µ C4 column (Phenomenex, Torrance, Calif.). The amino acids of the purified FGF-$1_{R136K}$ mutant FGF-1 protein were confirmed by sequence analysis.

The sequences for wild-type FGF-1 protein (SEQ ID NO:2), mutated FGF-1 protein, FGF-$1_{R136K}$, (SEQ ID NO:4), and the full length DNA sequence for wild type FGF-1 (SEQ ID NO:1) are provided herein and aligned to allow comparison of the sequences (see FIG. 1). Moreover, each sequence is provided separately in FIG. 8 (SEQ ID NO:1), FIG. 9 (SEQ ID NO:2), FIG. 10 (SEQ ID NO:3), and FIG. 11 (SEQ ID NO:4).

Cell Culture and Cell Proliferation Assays

To compare the biological activity of FGF-$1_{R136K}$ to wild type FGF-1 a proliferation assay using murine NIH 3T3 fibroblasts and a growth assay using bovine aortic endothelial cells were used.

Murine NIH 3T3 Cells and Tritiated-Thymidine Incorporation

Tritiated-thymidine ([$^3$H]-thymidine) incorporation studies using NIH 3T3 fibroblast cells were initially performed. The incorporation of [$^3$H]-thymidine into DNA is routinely used as an indicator of cell proliferation. 3T3 cells were grown to approximately 70% confluence in medium containing 10% calf serum and were then refed with low serum starvation medium (0.5% calf serum). Cells were incubated for 30 hours in the starvation medium. Following serum-starvation, cells were stimulated to proliferate with growth factors. Growth factors were diluted in Dulbecco's Modified Eagle's Medium (DMEM)+1% BSA±5 U/ml heparin and incubated with the cells for 18 hours. In some studies, the growth factor was pretreated in the presence of 10 U/ml thrombin for 24 hours. The cells were then pulsed with [$^3$H]-thymidine (0.5 µCi/well) and incorporation proceeded for 6 hours. The medium was removed and the cells were washed with saline. The cells were fixed in 100% methanol for 10 minutes, lysed with distilled water, and precipitated with 5% trichloroacetic acid. The cell lysates were washed with distilled water and the DNA was solubilized by adding 100 µl of 0.3 M NaOH. This solution was placed into 10 ml of scintillation fluid that contained 20 µl of acetic acid to avoid opacification of the scintillation fluid and counts per minute (cpm) were measured. Growth Factor-Induced Proliferation of Bovine Aortic Endothelial Cells Bovine aortic endothelial cells (BAEC) were isolated from bovine aortas by the collagenase dispersion method as previously described. All stock cultures of BAEC were grown in DMEM supplemented with 5% calf serum, penicillin (100 units/ml), streptomycin (100 µg/ml) and glutamine (100 mmol/ml). The culture medium was changed every 48 hours. All cultures were incubated in a humidified atmosphere of 10% $CO_2$ at 37° C. Cells were passaged by trypsinization.

BAECs were used to test the biological activity of FGF-$1_{R136K}$ compared to that of the wild-type form of FGF-1. Biological activity was tested in a growth assay that measured BAEC cell number. BAECs were plated at 20,000 cells/well into 6-well plates using DMEM containing 10% calf serum. The plating medium was replaced 24 hours later with starvation medium (DMEM containing 0.5% serum) and the BAECs were growth-arrested by serum-starvation for 24 hours. Various amounts of wild-type FGF-1, FGF-$1_{R136K}$, and heparin were added to DMEM containing 2.5% calf serum, which was then used to grow the cells. In other studies the growth factor (50 ng/ml), with or without 10 µg/ml heparin, was preincubated in the presence of various amounts of thrombin. After 2 hours at 37° C., thrombin activity was stopped by the addition of hirudin (an amount equivalent to the amount of thrombin added) and this mixture was added to the BAECs. The number of BAECs in some of the wells was determined at this time (day 0) using a Coulter counter. After 3 days of incubation the BAECs in each well were trypsinized and counted using a Coulter counter. Each experimental condition was performed in triplicate.

Methods to Determine Degradation Resistance

Western Blot Analyses for Degradation of Proteins and Peptides

Western blot analyses were performed using standard techniques. Wild-type FGF-1 and FGF-$1_{R136K}$ were each incubated in various concentrations of thrombin, in the presence or absence of heparin, for 2 hours at 37° C. Samples were then subjected to SDS-PAGE. Separation was performed utilizing a 4% polyacrylamide stacking gel and a 15% polyacrylamide running gel. The proteins were then transferred to PVDF membranes. The membranes were incubated with polyclonal antibodies against FGF-1 and the FGF-bound antibodies were then visualized by chemiluminescence.

The Results of the experiments presented in this example are now described.

Site directed mutagenesis was used to generate a mutant FGF-1 which is less susceptible to thrombin degradation. More specifically, site directed mutagenesis was used to generate a single amino acid change in the recombinant human FGF-1 protein sequence. Specifically, the arginine at position 136 was changed to lysine. FIG. 1 depicts the nucleic (SEQ ID NO: 1) and amino (SEQ ID NO:2) acid sequence of human wild type FGF-1, as well as the nucleic (SEQ ID NO:3) and amino (SEQ ID NO:4) acid sequence of mutant FGF-1$_{R136K}$.

The data disclosed herein demonstrate that the resulting mutant, FGF-1$_{R136K}$, retained the biological activity of wild-type FGF-1, but was less sensitive to thrombin cleavage than wild-type FGF-1. Thus, the thrombin-resistant FGF-$1_{R136K}$ mutant is an ideal candidate for an enhanced therapeutic form of FGF-1. More specifically, wild-type FGF-1 and the FGF-1 mutant FGF-$1_{R136K}$ were both tested for their ability to stimulate NIH 3T3 cell proliferation. Each was tested in the presence or absence of heparin and thrombin. Both growth factors were found to have increased mitogenic activity in the presence of heparin.

The data disclosed herein demonstrates that wild-type FGF-1 growth stimulating activity was decreased by pre-treating it with thrombin (FIG. 2). However, FGF-$1_{R136K}$ growth stimulating activity actually increased following thrombin pretreatment (FIG. 3). Thus, the data demonstrate that FGF-$1_{R136K}$, like wild-type FGF-1, is a more effective mitogen when administered in the presence of heparin, but, surprisingly, the mutant FGF-1 has increased biological activity on fibroblasts following treatment with thrombin.

The data disclosed herein also illustrate that not only can a mutant FGF-1 maintain biological activity following treatment with a degradation agent such as thrombin, but the data also demonstrate the unexpected result that biological activity of a mutant FGF-1 can be increased by treatment with an agent which normally degrades wild-type FGF-1 (see, e.g., FIGS. 2 and 3). These data suggest that the mutation of FGF-1 actually has at least a two fold effect on the mutant. First, the mutant FGF-1 FGF-$1_{R136K}$ is resistant to thrombin degradation and the amount of FGF-$1_{R136K}$ administered to a subject can maintain an effectively higher concentration of biologically active molecules than wild-type FGF-1 in similar circumstances. In addition, the biological activity itself is greater in the mutant once exposed to thrombin. Thus, not only is the mutant FGF-$1_{R136K}$ resistant to the negative effects of thrombin on biological activity, its activity actually increases following exposure to thrombin.

The glycosaminoglycan heparin is known to enhance the mitogenic activity of FGF-1. As demonstrated previously elsewhere herein, heparin can also enhance the mitogenic activity of FGF-$1_{R136K}$. Next, it was determined whether heparin could enhance FGF-$1_{R136K}$ activity in a dose-dependent fashion. Because FGF-1 is a growth factor that can elicit effects from many cell types, it was decided to compare the effects of FGF-1 and the FGF-1 mutant FGF-$1_{R136K}$ on the proliferation of another cell type, namely bovine aortic endothelial cells (BAEC), which are known to be sensitive to the mitogenic effects of FGF-1. Either FGF-1 or FGF-$1_{R136K}$, in the presence or absence of heparin, was added to BAEC which had been growth-arrested by serum starvation.

The results described herein show that FGF-1 and FGF-$1_{R136K}$ had very similar effects on BAEC proliferation as measured three days after addition of the growth factor (FIG. 4). The effects of FGF-1 and FGF-$1_{R136K}$ on BAEC proliferation were similar in the absence and presence of various amounts of heparin (FIG. 4). The results obtained when using the growth factors at either 5 ng/ml or 50 ng/ml were similar for both FGF-1 and FGF-$1_{R136K}$. The data disclosed herein demonstrate that both FGF-1 and FGF-$1_{R136K}$ induced only moderate proliferation of BAECs in the absence of heparin.

The amount of proliferation increased with increasing concentrations of heparin. More specifically, peak activity was detected in the presence of 1 $\mu$g/ml heparin added to 5 ng/ml FGF-1 or FGF-$1_{R136K}$ and with 10 $\mu$g/ml of heparin added to 50 ng/ml of FGF-1 or FGF-$1_{R136K}$. However, higher concentrations of heparin reduced proliferation. Without wishing to be bound by any particular theory, heparin inhibition of proliferation at higher doses suggests that excess soluble heparin competed with the cell surface heparan sulfate binding of FGF-1 or FGF-$1_{R136K}$ and prevented the growth factor from binding to the cell surface. Exposure of cells to up to 100 $\mu$g/ml heparin in the absence of growth factors caused no cell proliferation.

The data disclosed previously elsewhere herein demonstrates that FGF-$1_{R136K}$ had biological activity and that the activity was enhanced in the presence of heparin. Based on these results, experiments were performed to determine how similar the growth stimulating ability of the mutant FGF-1 protein FGF-$1_{R136K}$ was to its parent, wild-type FGF-1. BAEC were allowed to undergo growth arrest by serum deprivation. Then, the BAEC were exposed to varied concentrations of wild-type FGF-1 or FGF-$1_{R136K}$, in the absence or presence of 10 $\mu$g/ml heparin, and dose response curves were generated. Overall, FGF-1 and FGF-$1_{R136K}$ displayed similar degrees of BAEC proliferation-stimulating activity, both in the absence and presence of heparin (FIG. 5). As was also demonstrated by the data disclosed previously elsewhere herein, the proliferation-stimulating activity of FGF-$1_{R136K}$ was enhanced in the presence of heparin (FIG. 5). Thus, based on cell proliferation assays, the mutated derivative of FGF-1, FGF-$1_{R136K}$, was not only biologically active, but it also had mitogenic activity levels similar to that of the parent FGF-1.

Increased Resistance to Thrombin Degradation

As pointed out elsewhere herein, wild-type (native) FGF-1 is susceptible to thrombin degradation, which results in decreased biological activity. The resultant decreased biological activity concomitantly decreases FGF-1 utility in some disease or injury situations where FGF-1 is required to exert an effect. FGF-1 is an extremely potent mitogen and could have potentially great benefit because of its ability to stimulate angiogenesis, wound healing, regeneration, and morphogenesis. Nevertheless, until the present invention, its susceptibility to thrombin degradation diminished FGF-1's ability to act positively in these processes.

Experiments were performed to determine whether FGF-$1_{R136K}$, was less susceptible to thrombin degradation than wild-type FGF-1. This set of experiments was specifically designed to compare the effects of thrombin on the biological activity of FGF-$1_{R136K}$, to its effects on the biological activity of wild-type FGF-1.

The present invention discloses that the biological activity of FGF-$1_{R136K}$ following treatment with thrombin differed greatly from that of wild-type FGF-1 also treated with thrombin (FIG. 6).

Growth factors (10 ng/ml), in the absence or presence of 10 $\mu$g/ml heparin, were pretreated in the presence of various amounts of thrombin. After incubation for 2 hours, hirudin was added to stop the thrombin activity. The treated growth factors were added to growth stimulating base medium for and fed to BAECs. The cells were counted 3 days later. The data disclosed herein demonstrate that the parental FGF-1 was very susceptible to thrombin degradation and that most of its activity was lost when incubated with as little as 1 U/ml thrombin. The addition of heparin only marginally protected the FGF-1. In contrast, FGF-$1_{R136K}$ was much more resistant to thrombin degradation and the resistance was even more evident in the presence of heparin.

Because of differences between wild-type FGF-1 and FGF-1$_{R136K}$ growth factor activity following thrombin treatment, it was next determined whether the mutant FGF-1 protein, FGF-1$_{R136K}$, was susceptible to thrombin degradation. More specifically, wild-type FGF-1 and FGF-1$_{R136K}$ were incubated separately in various concentrations of thrombin for 2 hours at 37° C., in the presence or absence of heparin. At the end of the incubation period the treated growth factors were subjected to SDS-PAGE. Electrophoretic separation was performed using a 15% running gel with a 4% stacking gel. Subsequently, proteins were transferred by Western blotting to PVDF membranes and then FGF-1 proteins were immunostained using polyclonal antibodies raised against FGF-1. The antibody-bound FGF proteins were visualized by chemiluminescence.

The degradation of wild-type FGF-1 by thrombin was confirmed using Western blotting analyses (FIG. 7A and FIG. 7B). In the absence of heparin (FIG. 6A), wild-type FGF-1 was degraded by even the lowest concentration of thrombin used (0.5 U/ml) as demonstrated by the two bands detected in the Western blot at 17 kD and 14 kD. The addition of heparin delayed this degradation. In contrast, FGF-1$_{R136K}$, even in the absence of heparin, was relatively resistant to thrombin degradation (FIG. 7C and FIG. 7D).

Further, the data disclosed herein demonstrate that although wild type and thrombin resistant FGF-1 are apparently cleaved upon exposure to thrombin, the lower band of each doublet detected in the gel for each wtFGF-1 and mutant FGF-1 is at a different molecular mass. That is, the band detected upon treatment of FGF-1$_{R136K}$ mutant is slightly larger than the degradation band from wild type FGF-1. Thus, without wishing to be bound by any particular theory, the data disclosed herein demonstrate that although the mutant FGF-1$_{R136K}$ was cleaved by thrombin, the cleavage apparently occurs at a different site on the molecule compared with wild type FGF-1 and cleavage, unlike wtFGF-1, and does not affect biological activity of the mutant.

The data disclosed herein demonstrate that the thrombin-resistant FGF-1$_{R136K}$ mutant is more stable following treatment with thrombin than is wild-type FGF-1. This suggests that it can be used at lower concentrations but still exhibit high biological activity in areas where thrombin is present, such as, but not limited to, sites of injury or ischemia. This mutant FGF-1, and derivatives, fragments, and variants thereof, has the potential to be used as an angiogenic factor and potential nerve regenerator. Further, the skilled artisan would appreciate that there is a wide plethora of uses for FGF-1 resistant to thrombin degradation, and such uses need not be set forth herein.

These surprising results discussed previously herein, i.e., that a single amino acid substitution at a site apparently involved in heparin binding resulted in a polypeptide highly resistant to thrombin cleavage, is even more remarkable in that the amino acid substitution is a conservative change from arginine to lysine. These results are unprecedented in the prior art and could not have been predicted based on any prior art knowledge regarding either FGF-1 and/or thrombin cleavage. In addition, and without wishing to be bound by any particular theory, these data demonstrate that other amino acid substitutions at amino acid residue number 136 relative to the sequence of SEQ ID NO:2, can also produce mutant proteins resistant to thrombin cleavage. This is particularly true given that other substitutions are even more radical changes than the highly conservative substitution of lysine in place of arginine.

The data disclosed herein demonstrate, for the first time, the identification and production of a mutant FGF-1 that is highly resistant to thrombin degradation. Remarkably, this mutant FGF-1 has greater activity than the wild type molecule and is essentially impervious to degradation by thrombin, making the mutant form of FGF-1 an ideal candidate for delivery of active FGF-1 to a site of interest.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. An isolated nucleic acid encoding a fibroblast growth factor-1 resistant to thrombin degradation, wherein said nucleic acid comprises the sequence of SEQ ID NO:3.

2. An isolated nucleic acid encoding a fibroblast growth factor-1 resistant to thrombin degradation, wherein said nucleic acid comprises the sequence of SEQ ID NO: 1 and further wherein the triplet set of nucleotides CGG at position number 443 to 445 in SEQ ID NO: 1 is substituted with a triplet set of nucleotides selected from the group consisting of AAA and AAG.

3. An isolated nucleic acid encoding a fibroblast growth factor-1 resistant to thrombin degradation, wherein said nucleic acid comprises the sequence of SEQ ID NO: 1 and further wherein the triplet set of nucleotides CGG at position number 443 to 445 in SEQ ID NO: 1 is substituted with the triple set of nucleotides AAA.

4. An isolated nucleic acid encoding a fibroblast growth factor-1 resistant to thrombin degradation, wherein said nucleic acid comprises the sequence of SEQ ID NO: 1 and further wherein the triplet set of nucleotides at position number 443 to 445 in SEQ ID NO: 1 is not CGG, CGT, CGC, CGA, AGA, or AGG.

5. An isolated nucleic acid encoding a fibroblast growth factor-1 resistant to thrombin degradation, wherein said nucleic acid consists of the sequence of SEQ ID NO:3.

6. An isolated nucleic acid encoding a fibroblast growth factor-1 resistant to thrombin degradation, wherein said nucleic acid encodes a polypeptide comprising the amino acid sequence of SEQ ID NO:4.

7. An isolated nucleic acid encoding a fibroblast growth factor-1 resistant to thrombin degradation, wherein said nucleic acid encodes a polypeptide wherein said polypeptide comprises the amino acid sequence set forth in SEQ ID NO:2, further wherein the amino acid residue at position number 136 in the amino acid sequence set forth in SEQ ID NO:2 is lysine.

8. An isolated nucleic acid encoding a fibroblast growth factor-1 resistant to thrombin degradation, wherein said nucleic acid encodes a polypeptide wherein said polypeptide comprises the amino acid sequence set forth in SEQ ID NO:2, further wherein the amino acid residue at position number 136 in the amino acid sequence set forth in of SEQ ID NO:2 is not arginine.

9. An isolated nucleic acid encoding a fibroblast growth factor-1 resistant to thrombin degradation, wherein said nucleic acid encodes a polypeptide consisting of the amino acid sequence of SEQ ID NO:4.

10. The isolated nucleic acid of claim 1, wherein said nucleic acid comprises a nucleic acid specifying a promoter/regulatory sequence operably linked thereto.

11. A vector comprising the isolated nucleic acid of claim 1.

12. The vector of claim 11, said vector further comprising a nucleic acid specifying a promoter/regulatory sequence operably linked thereto.

13. A isolated recombinant cell comprising the vector of claim 11.

14. A isolated recombinant cell comprising the vector of claim 12.

15. The isolated recombinant cell of claim 13, wherein said cell is selected from a prokaryotic cell, and a eukaryotic cell.

16. A isolated recombinant cell comprising the isolated nucleic acid of claim 1.

17. The isolated recombinant cell of claim 15, wherein said recombinant cell is a mammalian cell.

18. A composition comprising an isolated nucleic acid encoding a fibroblast growth factor-1 resistant to thrombin degradation, wherein the nucleic acid comprises the sequence of SEQ ID NO:3, and a pharmaceutically acceptable carrier.

* * * * *

SEQUENCE LISTING

```
<160> NUMBER OF SEQ ID NOS: 8

<210> SEQ ID NO 1
<211> LENGTH: 638
<212> TYPE: DNA
<213> ORGANISM: Homo sapiens

<400> SEQUENCE: 1
gaattcggga acgcgccaca agcagcagct gctgagccat ggctgaaggg gaaatcacca        60
ccttcacagc cctgaccgag aagtttaatc tgcctccagg gaattacaag aagcccaaac       120
tcctctactg tagcaacggg ggccacttcc tgaggatcct tccggatggc acagtggatg       180
ggacaaggga caggagcgac cagcacattc agctgcagct cagtgcggaa agcgtggggg       240
aggtgtatat aaagagtacc gagactggcc agtacttggc catggacacc gacgggcttt       300
tatacggctc acagacacca aatgaggaat gtttgttcct ggaaaggctg gaggagaacc       360
attacaacac ctatatatcc aagaagcatg cagagaagaa ttggtttgtt ggcctcaaga       420
agaatgggag ctgcaaacgc ggtcctcgga ctcactatgg ccagaaagca atcttgtttc       480
```

```
tcccctgcc agtctcttct gattaaagag atctgttctg gtgttgacca ctccagagaa    540
gtttcgaggg gtcctcacct ggttgacccc aaaaatgttc ccttgaccat tggctgcgct    600 aaccccagc ccacagagcc tgaatttgta agcaactt                              638
```

<210> SEQ ID NO 2
<211> LENGTH: 154
<212> TYPE: PRT
<213> ORGANISM: Homo sapiens

<400> SEQUENCE: 2

```
Ala Glu Gly Glu Ile Thr Thr Phe Thr Ala Leu Thr Glu Lys Phe Asn
1               5                   10                  15

Leu Pro Pro Gly Asn Tyr Lys Lys Pro Lys Leu Leu Tyr Cys Ser Asn
            20                  25                  30

Gly Gly His Phe Leu Arg Ile Leu Pro Asp Gly Thr Val Asp Gly Thr
        35                  40                  45

Arg Asp Arg Ser Asp Gln His Ile Gln Leu Gln Leu Ser Ala Glu Ser
    50                  55                  60

Val Gly Glu Val Tyr Ile Lys Ser Thr Glu Thr Gly Gln Tyr Leu Ala
65                  70                  75                  80

Met Asp Thr Asp Gly Leu Leu Tyr Gly Ser Gln Thr Pro Asn Glu Glu
                85                  90                  95

Cys Leu Phe Leu Glu Arg Leu Glu Glu Asn His Tyr Asn Thr Tyr Ile
            100                 105                 110

Ser Lys Lys His Ala Glu Lys Asn Trp Phe Val Gly Leu Lys Lys Asn
        115                 120                 125

Gly Ser Cys Lys Arg Gly Pro Arg Thr His Tyr Gly Gln Lys Ala Ile
    130                 135                 140

Leu Phe Leu Pro Leu Pro Val Ser Ser Asp
145                 150
```

<210> SEQ ID NO 3
<211> LENGTH: 638
<212> TYPE: DNA
<213> ORGANISM: Homo sapiens

<400> SEQUENCE: 3

```
gaattcggga acgcgccaca agcagcagct gctgagccat ggctgaaggg gaaatcacca    60
ccttcacagc cctgaccgag aagtttaatc tgcctccagg gaattacaag aagcccaaac   120
tcctctactg tagcaacggg ggccacttcc tgaggatcct tccggatggc acagtggatg   180
ggacaaggga caggagcgac cagcacattc agctgcagct cagtgcggaa agcgtggggg   240
aggtgtatat aaagagtacc gagactggcc agtacttggc catggacacc gacgggcttt   300
tatacggctc acagacacca aatgaggaat gtttgttcct ggaaaggctg gaggagaacc   360
attacaacac ctatatatcc aagaagcatg cagagaagaa ttggtttgtt ggcctcaaga   420
agaatgggag ctgcaaacgc ggtcctaaaa ctcactatgg ccagaaagca atcttgtttc   480 tcccctgcc agtctcttct gattaaagag atctgttctg gtgttgacca ctccagagaa    540
gtttcgaggg gtcctcacct ggttgacccc aaaaatgttc ccttgaccat tggctgcgct    600 aaccccagc ccacagagcc tgaatttgta agcaactt                              638
```

<210> SEQ ID NO 4
<211> LENGTH: 154
<212> TYPE: PRT

<213> ORGANISM: Homo sapiens

<400> SEQUENCE: 4

```
Ala Glu Gly Glu Ile Thr Thr Phe Thr Ala Leu Thr Glu Lys Phe Asn
 1               5                  10                  15
Leu Pro Pro Gly Asn Tyr Lys Pro Lys Leu Leu Tyr Cys Ser Asn
                20                  25                  30
Gly Gly His Phe Leu Arg Ile Leu Pro Asp Gly Thr Val Asp Gly Thr
                35                  40                  45
Arg Asp Arg Ser Asp Gln His Ile Gln Leu Gln Leu Ser Ala Glu Ser
        50                  55                  60
Val Gly Glu Val Tyr Ile Lys Ser Thr Glu Thr Gly Gln Tyr Leu Ala
65                  70                  75                  80
Met Asp Thr Asp Gly Leu Leu Tyr Gly Ser Gln Thr Pro Asn Glu Glu
                85                  90                  95
Cys Leu Phe Leu Glu Arg Leu Glu Glu Asn His Tyr Asn Thr Tyr Ile
                100                 105                 110
Ser Lys Lys His Ala Glu Lys Asn Trp Phe Val Gly Leu Lys Lys Asn
            115                 120                 125
Gly Ser Cys Lys Arg Gly Pro Arg Thr His Tyr Gly Gln Lys Ala Ile
        130                 135                 140
Leu Phe Leu Pro Leu Pro Val Ser Ser Asp
145                 150
```

<210> SEQ ID NO 5
<211> LENGTH: 31
<212> TYPE: DNA
<213> ORGANISM: Artificial Sequence
<220> FEATURE:
<223> OTHER INFORMATION: PCR primer

<400> SEQUENCE: 5
caaacgcggt cctcggactc actatggcca g        31

<210> SEQ ID NO 6
<211> LENGTH: 10
<212> TYPE: PRT
<213> ORGANISM: Artificial Sequence
<220> FEATURE:
<223> OTHER INFORMATION: Amino acid encoded by PCR primer

<400> SEQUENCE: 6

```
Lys Arg Gly Pro Arg Thr His Tyr Gly Gln
 1               5                  10
```

<210> SEQ ID NO 7
<211> LENGTH: 31
<212> TYPE: DNA
<213> ORGANISM: Artificial Sequence
<220> FEATURE:
<223> OTHER INFORMATION: PCR primer

<400> SEQUENCE: 7
caaacgcggt cctaaaactc actatggcca g        31

<210> SEQ ID NO 8
<211> LENGTH: 10
<212> TYPE: PRT
<213> ORGANISM: Artificial Sequence
<220> FEATURE:
<223> OTHER INFORMATION: PCR primer -continued

```
<400> SEQUENCE: 8

Lys Arg Gly Pro Arg Thr His Tyr Gly Gln
1               5                   10
```